US011439115B2

(12) United States Patent
Pontes et al.

(10) Patent No.: US 11,439,115 B2
(45) Date of Patent: Sep. 13, 2022

(54) HYBRID TOBACCO PLANTS FROM CROSSES BETWEEN FLUE-CURED AND AIR-CURED TOBACCO TYPES

(71) Applicant: BRITISH AMERICAN TOBACCO (INVESTMENTS) LIMITED, London (GB)

(72) Inventors: Oscar Francisco Swenson Pontes, Rio de Janeiro (BR); Carlos Pulcinelli, Rio de Janeiro (BR)

(73) Assignee: British American Tobacco (Investments) Limited, London (GB)

( * ) Notice: Subject to any disclaimer, the term of this patent is extended or adjusted under 35 U.S.C. 154(b) by 80 days.

(21) Appl. No.: 16/630,072

(22) PCT Filed: Jul. 10, 2018

(86) PCT No.: PCT/GB2018/051945
§ 371 (c)(1),
(2) Date: Jan. 10, 2020

(87) PCT Pub. No.: WO2019/012261
PCT Pub. Date: Jan. 17, 2019

(65) Prior Publication Data
US 2020/0229370 A1 Jul. 23, 2020

(30) Foreign Application Priority Data
Jul. 11, 2017 (GB) ..................................... 1711132

(51) Int. Cl.
*A01H 5/10* (2018.01)
*A01H 6/82* (2018.01)
*A01H 5/12* (2018.01)
*A24B 13/00* (2006.01)
*A24B 15/10* (2006.01)

(52) U.S. Cl.
CPC ............... *A01H 6/823* (2018.05); *A01H 5/10* (2013.01); *A01H 5/12* (2013.01); *A24B 13/00* (2013.01); *A24B 15/10* (2013.01)

(58) Field of Classification Search
CPC .................................. A01H 6/823; A01H 5/10
See application file for complete search history.

(56) References Cited

U.S. PATENT DOCUMENTS

| 2,162,738 A | 6/1939 | Mccoy |
| 7,700,834 B2 | 4/2010 | Xu et al. |
| 9,370,160 B2 | 6/2016 | Xu et al. |
| 2008/0209586 A1 | 8/2008 | Nielsen et al. |

FOREIGN PATENT DOCUMENTS

| AU | 2011232795 B2 | 11/2011 |
| GB | 2515502 A | 12/2014 |
| WO | 2004041006 A1 | 5/2004 |
| WO | 2010147467 A2 | 12/2010 |
| WO | 2013034459 A1 | 3/2013 |
| WO | 2013034460 A1 | 3/2013 |
| WO | 2015077197 A1 | 5/2015 |

OTHER PUBLICATIONS

Nielsen and Severson, J. Agric. Food Chem. (1990) 38:467-471. (Year: 1990).*
Danehower, D.A., et al. Tob. Sci. (1988) 32:49-52. (Year: 1988).*
Wahlberg, I. et al. Acta Chemica Scandinavica B 33 (1979) pp. 541-543. (Year: 1979).*
Tomita, H. et al. Agric. Biol. Chem., (1980) vol. 44, No. 10; pp. 2517-2518. (Year: 1980).*
Tomita et al., "Inheritance of Labdanoid Producing Ability in Nicotiana tabacum", Agric. Biol. Chem., vol. 44(10), pp. 2517-2518, 1980.
Vontimitta et al., "Analysis of a *Nicotiana tabacum* L. Genomic Region Controlling Two Leaf Surface Chemistry Traits", J. Agric. Food Chem., vol. 58, pp. 294-300, 2010.
Foulds et al., "Effect of smokeless tobacco (snus) on smoking and public health in Sweden", Tobacco Control, vol. 12, pp. 349-359, Oct. 2, 2003.
Gwynn et al., "Inheritance of sucrose esters containing B-methylvaleric acid in tobacco", Tobacco Science, 4 pages, Jan. 1985.
Hale & Margham, "The Harper Collins Dictionary of Biology", Harper Perennial, 576 pages, Mar. 1, 1991.
Weckwerth and Kahl, "The Handbook of Plant Metabolomics", Wiley-Blackwell, 610 pages, May 28, 2013.
Neilsen et al., "Registration of KDH 926, KDH 959, KDH 960 Tobacco Germplasm Lines with Different Levels of Trichome Exudate Constitutents", Crop Science, vol. 29, pp. 1584-1585, Nov. 1989.
Sallaud et al., "Characterization of two genes for the biosynthesis of the labdane diterpene Z-abienol in tobacco (*Nicotiana tabacum*) glandular trichomes", The Plant Journal, vol. 72, pp. 1-17, May 23, 2012.
Singleton et al., Dictionary of Microbiology and Molecular Biology, Wiley-Blackwell, 1032 pages, Dec. 16, 1987.
Wahlberg et al., "Tobacco Isoprenoids", Natural Product Reports, pp. 237-276, 1987.
Wernsman et al., "Tobacco", Principles of cultivar development, ch. 17, pp. 669-698, 1987.
Whitfield, Matthew, "Integrated Bioprocessing of Native and Engineered Components from Tobacco (*Nicotiana tabacum* L.)", Thesis for Degree of Master of Science, North Carolina State University, 127 pages, Mar. 17, 2017.

* cited by examiner

*Primary Examiner* — Russell Kallis
(74) *Attorney, Agent, or Firm* — McKee, Voorhees & Sease, PLC

(57) ABSTRACT

The present invention provides a cured hybrid tobacco plant or a part thereof made between a parent flue-cured tobacco plant and a parent non-flue-cured tobacco plant; which cured hybrid tobacco plant or a part thereof comprises one or more flavour compounds which are a breakdown product of cis-abienol at a concentration which is about equal to or greater than the concentration in the cured parent non-flue-cured tobacco plant.

18 Claims, 10 Drawing Sheets

HYBRID TOBACCO PLANTS FROM CROSSES BETWEEN FLUE-CURED AND AIR-CURED TOBACCO TYPES

CROSS REFERENCE TO RELATED APPLICATIONS

This application is the National Stage of International Application No. PCT/GB2018/051945, filed Jul. 10, 2018, which claims priority to Great Britain Patent Application No. 1711132.9, filed Jul. 11, 2017, all of which are herein incorporated by reference in their entirety for all purposes.

FIELD OF THE INVENTION

The present invention relates to tobacco plants with commercially favourable characteristics and particular flavour profiles, their development via breeding; and plant cells, plant propagation material, harvested leaf, processed leaf or a product derived therefrom.

BACKGROUND

Different types of tobaccos are typically mixed at various ratios to form specific blends for use in tobacco products (see Fisher, Tobacco Blending, Chapter 11A Tobacco Production, Chemistry and Technology, Edited by L. Davis and M. Nielsen, Blackwell Sciences 1999). Organoleptic properties of different tobacco types or varieties vary considerably and are influenced by a complexity of factors including genetic differences. Further, different tobacco types are amenable to different propagation and processing procedures; and have different robustness to environmental challenges (e.g. pest and droughts).

Flue-cured tobacco is the most widely grown tobacco (40% of world tobacco production) and is also known as "Bright" or "Virginia" tobacco. Flue-cured leaf is characterised by a high sugar:nitrogen ratio. This ratio is enhanced by picking the leaf in an advanced stage of ripeness and by the curing process which allows certain chemical changes to occur in the leaf. The leaves are relatively large with the largest at midstalk. A well grown plant will be topped at a height of about 39 to 51 inches with 18-22 harvestable leaves. Yields average around 2200 lbs/acre with some in excess of 3000 lbs/acre. The leaves are harvested as they mature from the ground up.

Because of its wide commercial use, Virginia tobacco plants typically possess a range of commercially favourable characteristics, for example good agronomical performance, large yields and sustainability through robustness against pests and drought. However, Virginia (flue-cured) tobacco types have a limited flavour profile.

Other tobacco types such as air-cured (e.g. Burley, Maryland and Galpão) or fire-cured (e.g. dark) tobacco types offer alternative flavour profiles. These flavour profiles are important, for example, in the production of blended tobacco products. These flavour characteristics are the results of particular flavour compounds or the precursors for these compounds that are present at certain levels in the tobacco plants or cured leaf.

These other tobacco types do not typically offer the same commercially desirable traits and characteristics as the Virginia flue-cured tobaccos. There remains a need for tobaccos with the distinctive flavour characteristics not provided by Virginia flue-cured tobacco, but with the improved yields and other commercially desirable traits of Virginia flue-cured tobacco plants.

SUMMARY OF THE INVENTION

It has been surprisingly found that distinctive flavour characteristics can be combined with commercially desirable traits of Virginia flue-cured tobacco to produce a hybrid which provides cured tobacco with distinct flavour characteristics that can be used by tobacco blenders to produce tobacco products with superior aroma, taste and flavour characteristics sought after by consumers of tobacco products. In particular, it has been found that flavour characteristics associated with air-cured and fire-cured tobacco can be combined with characteristics of Virginia flue-cured tobacco plants to produce a hybrid which provides flavour characteristics of an air-cured or fire-cured tobacco under growing and processing conditions which are typically applied to flue-cured tobacco plants.

In particular, the present invention provides such tobacco types which are, for example, hybrids between flue-cured tobacco (e.g. flue-cured Virginia tobacco) and N. tabacum L. var. Galpão Comum.

According to one aspect the present invention provides a cured hybrid plant (e.g. an F1 hybrid plant) or a part thereof made between a parent flue-cured tobacco plant and a parent non flue-cured tobacco plant, which cured hybrid tobacco plant or a part thereof comprises one or more flavour compounds which are a breakdown product of cis-abienol at a concentration which is about equal to or greater than the concentration in the cured parent non-flue-cured tobacco plant.

In one embodiment the cured hybrid plant or part thereof according to the present invention is a flue-cured hybrid plant or part thereof.

In one embodiment the cured hybrid plant or part thereof according to the present invention is grown and processed (e.g. cured) under conditions that a flue-cured tobacco would be grown and processed. In one embodiment the present flue-cured hybrid plant or part thereof is grown and processed (e.g. cured) under similar conditions to the parent flue-cured tobacco.

In one embodiment, when comparing the composition of the hybrid (e.g. flue-cured hybrid) plant or part therefore according to the present invention with one or both of the parent tobaccos, the flue-cured parent tobacco plant is suitably one which has been flue-cured, whereas the non-flue-cured parent tobacco plant is suitably one that has been air-cured or fire-cured.

The present invention provides non-naturally existing tobacco plants.

The present invention yet further provides methods of producing, growing and further breeding of a hybrid (e.g. an F1 hybrid) of the present invention.

In another aspect the present invention provides a plant cell obtainable (e.g. obtained) by a method according to the present invention or from a hybrid of the present invention.

In a further aspect the present invention provides a plant
i) obtainable by a method of the invention; or
ii) comprising a cell of the present invention.

In another aspect the present invention provides a plant propagation material (e.g. a plant seed) obtainable from a hybrid plant according to the present invention.

In a further aspect the present invention provides a harvested leaf of a hybrid plant according to the present invention or obtainable from a plant propagated from a propagation material of the present invention or obtainable from a hybrid plant obtainable by a method of the present invention.

In another aspect the present invention provides a processed leaf (suitably a non-viable processed leaf, e.g. cured leaf):
a. obtainable (obtained) from a hybrid plant according to the present invention.
b. comprising a plant cell of the present invention;
b. obtainable from a hybrid plant obtainable from a method of the present invention;
c. obtainable from processing a hybrid plant of the present invention;
d. obtainable from a hybrid plant propagated from a plant propagation material of the present invention; or
e. obtainable by processing a harvested leaf of the present invention.

In another embodiment the present invention provides a tobacco product:
a. prepared from a hybrid plant according to the present invention or a part thereof (suitably a leaf harvested from the hybrid plant);
b. prepared from a hybrid plant or a part thereof (suitably a leaf harvested from the hybrid plant) obtained or obtainable by the method of the present invention;
c. prepared from a hybrid plant (suitably the leaves of said hybrid plant) propagated from a plant propagation material of the present invention;
d. prepared from a harvested leaf of a hybrid plant according to the present invention;
e. prepared from a processed tobacco leaf (e.g. cured leaf) of a hybrid plant according to the present invention; or
f. prepared from or comprising a tobacco plant extract obtained from a hybrid plant according to the present invention.

In a further aspect the present invention provides a plant extract of a hybrid plant according to the present invention or of a portion of said plant.

In a further aspect the present invention provides the use of a hybrid plant of the invention for breeding a plant.

In another aspect the present invention provides the use of a hybrid plant according to the present invention to grow a crop.

In another aspect the present invention provides the use of a hybrid plant according to the present invention to produce a leaf (e.g. a processed (suitably cured) leaf).

BRIEF DESCRIPTION OF THE DRAWINGS

Embodiments of the invention will now be described, by way of example only, with reference to accompanying drawings, in which.

DETAILED DESCRIPTION

Figure 1:
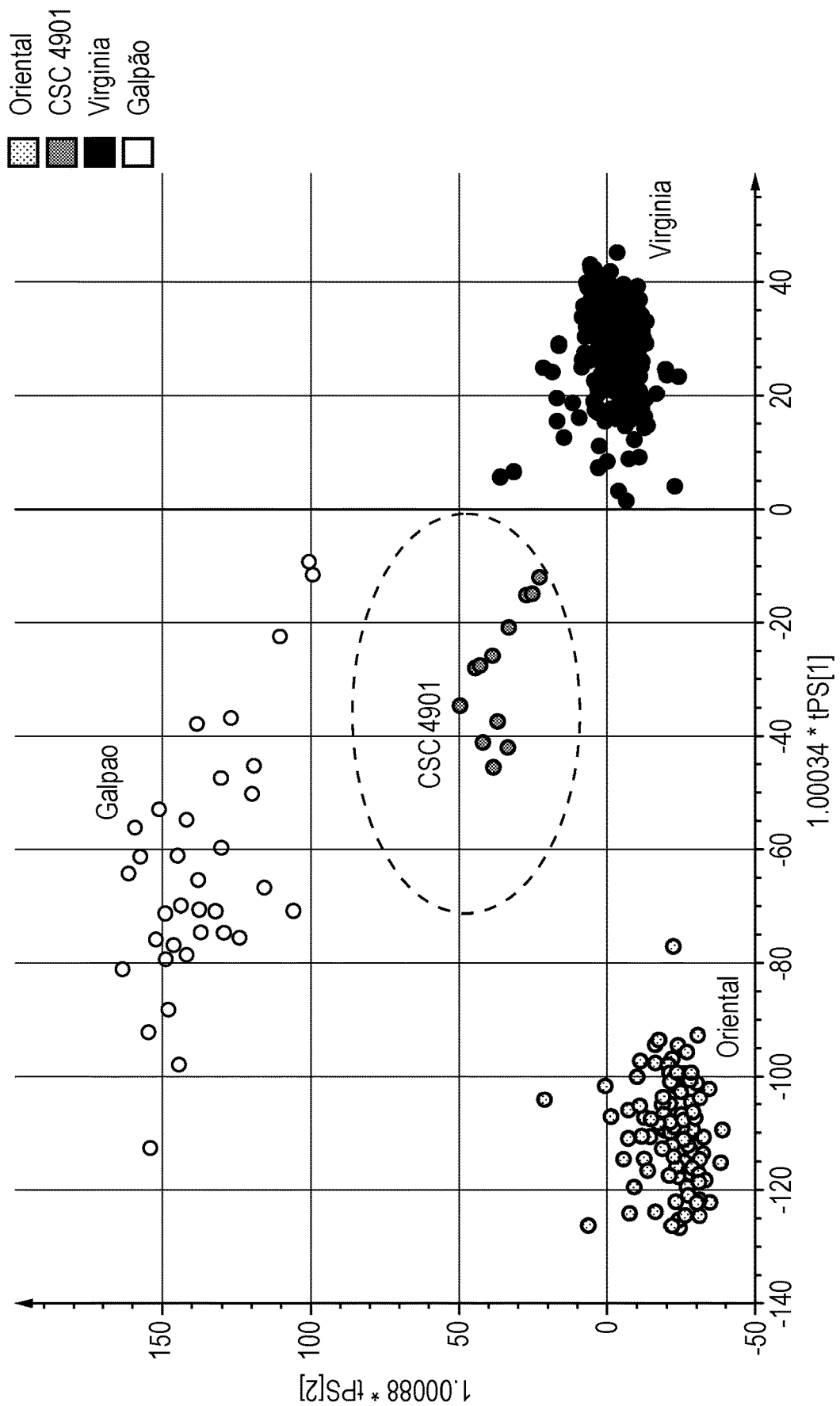
FIG. 1 illustrates the OPLS-DA score distribution plot for Galpao, Virginia, Oriental and CSC 4901 tobacco samples analyzed according to the HTS-FIA-HRMS methodology.

In one embodiment, the present hybrid tobacco plant or part thereof comprises one or more flavour compounds which are a breakdown product of cis-abienol at a concentration which is about equal to or greater than the concentration in the cured non flue-cured parent tobacco plant, and the hybrid plant further comprises one or more commercially desirable traits selected from the group consisting of drought resistance, pest resistance, mature plant height, harvestable leaf number, average node length, cutter leaf length, cutter leaf width, and yield comparable to those said traits in the flue-cured parent of the hybrid when grown under similar growth conditions. Preferably, the one or more commercially desirable traits is pest resistance.

As used herein, "about equal to" means that the concentration or ratio is approximately the same in the two subjects (e.g. the parent plant and hybrid plant) being compared. In particular, "about equal to" means that the concentration or ratio is comparable in the two subjects (e.g. the parent plant and hybrid plant) being compared. For example, the concentration or ratio may be less than 25% different, preferably less than 10% different, in the two subjects (e.g. the cured parent plant and cured hybrid plant) being compared. In one embodiment "about equal to" means "equal to".

As used herein, "greater than" means that the concentration or ratio is at least 1.5-fold greater, suitably at least 2-fold greater, in the present cured hybrid plant compared to the cured parent plant. In one embodiment "greater than" means about 2-fold greater than. In one embodiment "greater than" means 2-fold greater than.

Preferably, the cured hybrid tobacco plant or part thereof according to the present invention comprises one or more flavour compounds which are a breakdown product of cis-abienol at a concentration which is equal to or greater than the concentration in the cured non flue-cured parent tobacco plant.

Suitably, the hybrid plant or part thereof may be processed (e.g. cured) by any method, e.g. it may be flue-cured, air-cured, or fire-cured. In one embodiment the hybrid plant or part thereof may be processed by flue-curing.

Suitably, the concentration of the breakdown product of cis-abienol and/or total sucrose esters in the cured hybrid plant or a part thereof of the present invention may be about equal to (or equal to) or greater than the concentration in the non-flue-cured parent tobacco plant when the parent non flue-cured tobacco plant is grown and processed (e.g. cured) under typical conditions for said non-flue-cured tobacco. In other words, if the non flue-cured parent is an air-cured tobacco, it is cured by air-curing.

Suitably, the concentration of the breakdown product of cis-abienol in the cured hybrid plant or a part thereof of the present invention may be at least two-fold greater than the concentration in the parent non-flue-cured tobacco plant when grown and processed (e.g. cured) under typical conditions for said non-flue-cured tobacco. In other words, if the non flue-cured parent is an air-cured tobacco, it is cured by air-curing.

Suitably, the concentration of the breakdown product of cis-abienol and/or total sucrose esters in the cured hybrid plant or a part thereof of the present invention may be about equal to (or equal to) or greater than the concentration in the non-flue-cured parent tobacco plant when grown and processed (e.g. cured) under similar conditions.

Suitably, the concentration of the breakdown product of cis-abienol in the cured hybrid plant or a part thereof of the present invention may be at least two-fold greater than the concentration in the parent non-flue-cured tobacco plant when grown and processed (e.g. cured) under similar conditions.

Cis-Abienol

Cis-Abienol (also known as Z-Abienol) is a labdane diterpenoid in which the labdane skeleton has double bonds at C-12 and C-14 (the former with Z-stereochemistry) and carries a hydroxy group at position C-8. It is found in the tobacco leaf and has been shown to act as a plant growth regulator.

Structure of Cis-Abienol

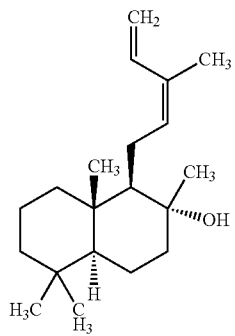 [SMILES: C=C/C(C)=C\C[C@@H]1[C@@]2(C)CCCC(C)(C)[C@@H]2CC[C@@]1(C)O]

During tobacco curing, cis-abienol is broken down into a number of breakdown products through various oxidative processes (as described in, for example, Wahlberg & Enzell; 1987; Nat. Prod. Rep.; 4(3); 237-79 which is hereby incorporated by reference).

Figure 9:
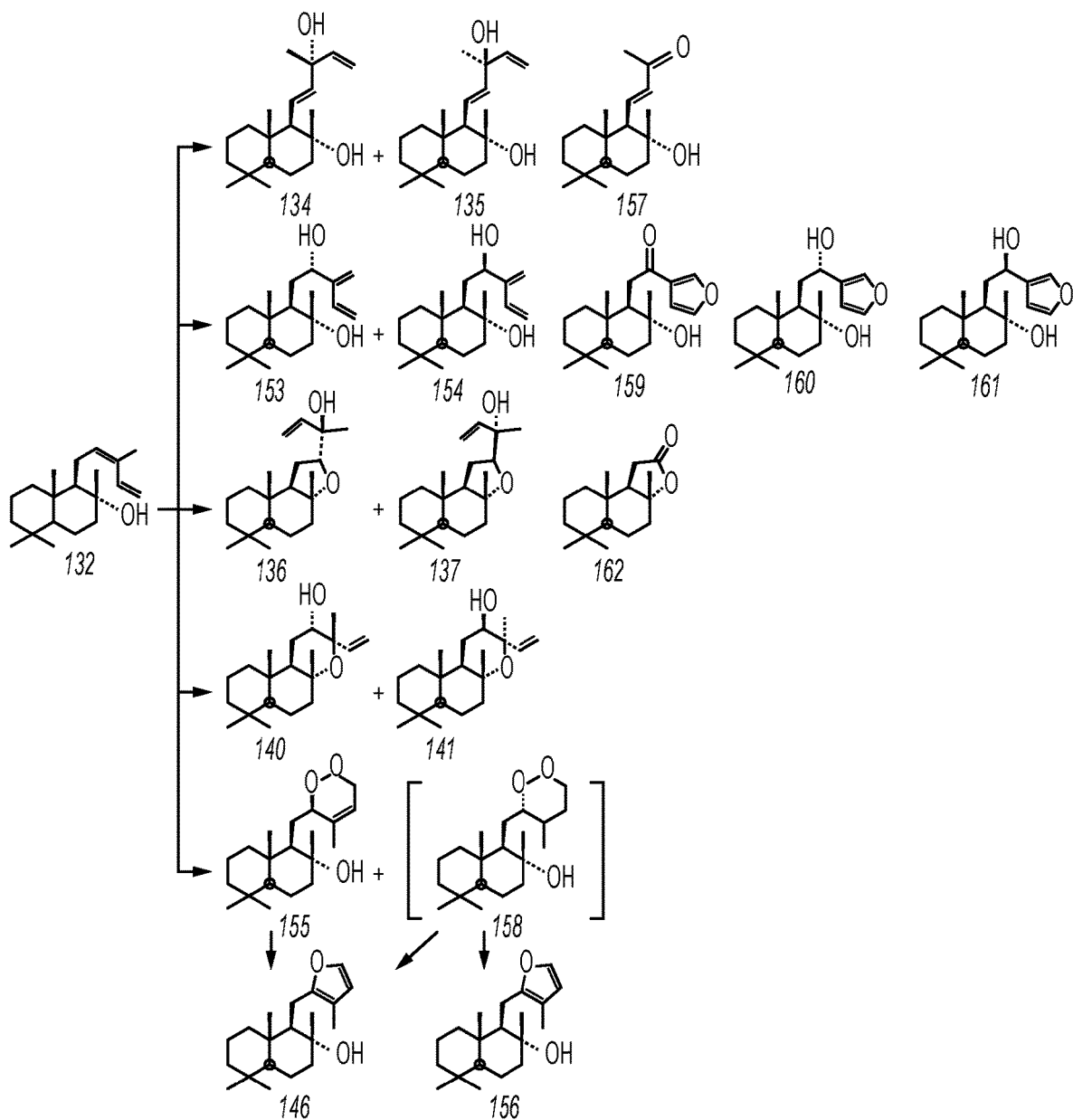
FIG. 9 shows breakdown products of cis-abienol.

For example, cis-abienol (see compound 132 in FIG. 9) reacts readily with singlet oxygen to give, after reduction of the initially generated hydroperoxides (using triphenylphosphine), compounds 134-137, 140, 141, 146, and 153-157 (see FIG. 9). These four compounds are formed by four competing processes. The predominant route (68%) is a syn-ene reaction, which takes place at the trisubstituted 12-13 double-bond in cis-abienol and gives, after reduction, the (8R,13R)- and (8R, 13S)-diols (134 and 135 in FIG. 9) in the ratio 1:2.

Consistent with the cis-cyclic mechanism, the hydroperoxide precursor of 135 may arise by attack of oxygen on C-13 and migration of the a-hydrogen at C-11 in a conformer of type a, whereas a reaction that occurs with conformer band involves the P-hydrogen at C-11 would yield the hydroperoxide precursor of 134 (see FIG. 9). The (8R,12S)- and (8R,12R)-diols (153 and 154 in FIG. 9) are also formed via ene reactions at the 12-13 double-bond, but oxygen is now attached to C-12 and a hydrogen at C-16 migrates. Conformer a is suggested to be the reacting species in the formation of the (12R)-12-hydroperoxide of labda-13 (16),14-dien-8-ol, whereas the corresponding (12S)-12-hydroperoxide would arise by reactions that took place with conformers b and c (FIG. 9). The two 8,1-2-diols (153 and 154 in FIG. 9) are minor products (3%); this result is consonant with their generation via anti-ene reactions.

The third process, accounting for some 12% of the overall yield, generates the (12R, 13R)- and (12S,13S)-8,12-epoxy-labd 14-en-13-01s 136 and 137 as well as the (12S,13S)- and (12R, 13R)-8,13-epoxylabd-14-en-12-01s (140 and 141 in FIG. 9).

Since these four compounds are also obtained by oxidation of cis-abienol by a peracid, it has been suggested that their formation involves attack of oxygen on the 12-13 double-bond and proceeds by anchimeric assistance of the 8a-hydroxyl group through peroxirane or epoxide types of intermediates. A conformer of type d would be the reacting species in the process leading to compounds 136 and 140 (as shown in FIG. 9), whereas the corresponding diastereoisomers 137 and 141 (as shown in FIG. 9) would be formed via conformer e.

Figure 10:
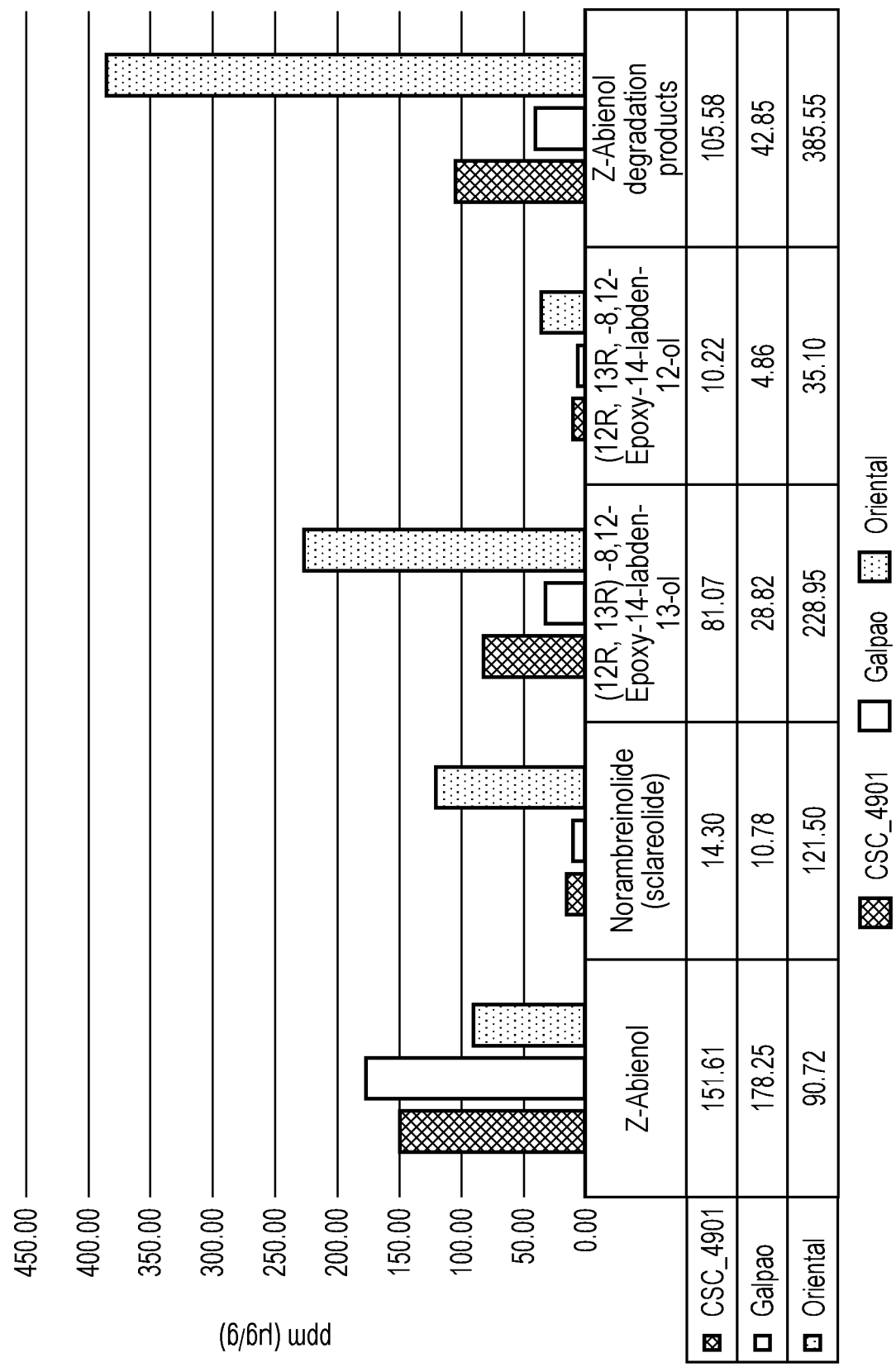
FIG. 10 shows the quantification of cis-abienol and its breakdown products using UPLC-HRMS

Suitably, the breakdown product of cis-abienol may be one or more compounds selected from norambreinolide, (12R, 13R)-8,12-Epoxy-14-labden-13-ol and (12R, 13R)-8,13-Epoxy-14-labden-12-ol, (11E,8R,13R)-labda-11,14-dien-8,13-diol, (11E,8R,13S)-labda-11,14-dien-8,13-diol, (8R,12S)-labda-13(16),14-dien-8,12-diol, (8R,12R)-labda-13(16),14-dien-8,12-diol, (8R,12S)-15,16-epoxylabda-13 (16),14-dien-8-ol, (8R,12R)-15,16-epoxylabda-13(16),14-dien-8-ol, (11E)-8-hydroxy-14,15-dinorlabd-11-en-13-one, (12S, 13S)-8,12-epoxylabd-14-en-13-ol, (12S, 13S)-8,13-epoxylabd-14-en-12-ol, (12R)-12,15-epidioxylabd-13-en-8-ol, (12S)-12,15-epidioxylabd-13-en-8-ol, 12,15-epoxy-labda-12,14-dien-8-ol, and (12S)-12,15-epoxylabd-13-en-8-ol. Suitably, the breakdown products of cis-abienol may be one or more of norambreinolide (shown as 162 in FIG. 10), (12R, 13R)-8,12-Epoxy-14-labden-13-ol and (12R, 13R)-8,13-Epoxy-14-labden-12-ol.

Suitably, the term "a breakdown product of cis-abienol" as used herein may mean one of the following compounds: norambreinolide, (12R, 13R)-8,12-Epoxy-14-labden-13-ol and (12R, 13R)-8,13-Epoxy-14-labden-12-ol.

In one embodiment the cured hybrid tobacco plant comprises more than one flavour compound which are breakdown products of cis-abienol. By way of example the cured hybrid tobacco plant may comprise two or more of the following compounds: norambreinolide, (12R, 13R)-8,12-Epoxy-14-labden-13-ol and (12R, 13R)-8,13-Epoxy-14-labden-12-ol.

In one embodiment the cured hybrid tobacco plant may comprise all three of the following compounds: norambreinolide, (12R, 13R)-8,12-Epoxy-14-labden-13-ol and (12R, 13R)-8,13-Epoxy-14-labden-12-ol.

In another aspect, the concentration of breakdown product(s) of cis-abienol in the present cured hybrid tobacco plant or a part thereof is at least 50-, 100-, 200-, 500-, 1000-, 10000-fold or more greater than the concentration of the breakdown product(s) of cis-abienol in the flue-cured parent of the hybrid.

In another aspect, the concentration of breakdown products of cis-abienol in the present cured hybrid tobacco plant or a part thereof are between about 100% and 250%, between 125% and 250%, between 150% and 250%, between 175% and 250%, between 100% and 225%, between 125% and 225%, between 150% and 225%, between 150% and 200%, or between 200% and 225% of the concentrations of the breakdown products of cis-abienol in the non flue-cured parent of the hybrid.

In one aspect, a hybrid tobacco plant of the present invention comprises one or more breakdown products of cis-abienol at a total concentration of at least about 2, at least about 3, at least about 4, at least about 5, at least about 10, at least about 15, at least about 20, at least about 25, at least about 30, at least about 35, at least about 40, at least about 45, at least about 50, at least about 60, at least about 70, at least about 80, at least about 90, at least about 100, at least about 125, at least about 150 or at least about 200 ppm (μg/g of tobacco, in particular μg/g of tobacco in wet basis).

In one embodiment, the breakdown products of cis-abienol may be one or more of norambreinolide, (12R, 13R)-8,12-Epoxy-14-labden-13-ol and (12R, 13R)-8,13-Epoxy-14-labden-12-ol and the total concentration of norambreinolide, (12R, 13R)-8,12-Epoxy-14-labden-13-ol and/or (12R, 13R)-8,13-Epoxy-14-labden-12-ol may be at least about 2, at least about 3, at least about 4, at least about 5, at least about 10, at least about 15, at least about 20, at least about 25, at least about 30, at least about 35, at least about 40, at least about 45, at least about 50, at least about 60, at least about 70, at least about 80, at least about 90, at least about 100, at least about 125, at least about 150 or at least about 200 ppm (μg/g of tobacco, in particular μg/g of tobacco in wet basis).

In one embodiment, the term "a breakdown product of cis-abienol" as used herein may mean one of the following compounds: norambreinolide, (12R, 13R)-8,12-Epoxy-14-labden-13-ol and (12R, 13R)-8,13-Epoxy-14-labden-12-ol and the concentration of any one of norambreinolide, (12R, 13R)-8,12-Epoxy-14-labden-13-ol or (12R, 13R)-8,13-Epoxy-14-labden-12-ol may be at least about 2, at least about 3, at least about 4, at least about 5, at least about 10, at least about 15, at least about 20, at least about 25, at least about 30, at least about 35, at least about 40, at least about 45, at least about 50, at least about 60, at least about 70, at least about 80, at least about 90, at least about 100, at least about 125, at least about 150 or at least about 200 ppm (μg/g of tobacco, in particular μg/g of tobacco in wet basis).

In one embodiment the cured hybrid tobacco plant may comprise all three of the following compounds: norambreinolide, (12R, 13R)-8,12-Epoxy-14-labden-13-ol and (12R, 13R)-8,13-Epoxy-14-labden-12-ol and the total concentration of norambreinolide, (12R, 13R)-8,12-Epoxy-14-labden-13-ol or (12R, 13R)-8,13-Epoxy-14-labden-12-ol at least about 2, at least about 3, at least about 4, at least about 5, at least about 10, at least about 15, at least about 20, at least about 25, at least about 30, at least about 35, at least about 40, at least about 45, at least about 50, at least about 60, at least about 70, at least about 80, at least about 90, at least about 100, at least about 125, at least about 150 or at least about 200 ppm (μg/g of tobacco, in particular μg/g of tobacco in wet basis).

In one embodiment the concentration of a breakdown product(s) of cis-abienol in the present cured hybrid tobacco plant or a part thereof is measured in processed (e.g. cured) tobacco or a processed (cured) part thereof (e.g. cured leaf). In particular, in one embodiment the concentration of breakdown products of cis-abienol in the present cured hybrid tobacco plant or a part thereof are measured in processed (e.g. flue-cured) tobacco or processed (e.g. flue-cured) tobacco leaf.

In one embodiment the present hybrid plant or a part thereof comprises one or more further flavour compounds at a concentration about equal to or greater than the concentration of said one or more further flavour compounds in the non-flue-cured parent. Suitably for analysis purposes with the hybrid plant of the present invention, the parent non-flue-cured tobacco plant may be grown and processed (e.g. cured) under typical conditions for said non-flue-cured tobacco or may be grown and processed (e.g. cured) under similar conditions to the present hybrid tobacco plant.

The hybrid plant or a part thereof may be a cured hybrid plant or a part thereof as described herein.

In one embodiment the one or more further flavour compounds may be selected from the group consisting of diterpenes, e.g. labdenoid diterprene, in particular cis-abienol; and/or sucrose esters, e.g. total sucrose esters, or β-methyl-valeric acid; and/or carotenoids and/or waxes and/or fatty acids.

In one embodiment the cured hybrid plant or a part thereof comprises one or more flavour compounds which are a breakdown product of cis-abienol at a concentration which is about equal to or greater than the concentration in the cured parent non-flue-cured tobacco plant and one or more flavour compounds selected from the group consisting of diterpenes, e.g. labdenoid diterpene, in particular cis-abienol; and/or sucrose esters, e.g. total sucrose esters, or β-methyl-valeric acid; and/or carotenoids and/or waxes and/or fatty acids at a concentration which is about equal to or greater than the parent non-flue-cured tobacco plant.

In one embodiment the cured hybrid plant or a part thereof comprises one or more flavour compounds which are a breakdown product of cis-abienol at a concentration which is about equal to or greater than the concentration in the cured parent non-flue-cured tobacco plant and a concentration of total sucrose esters at a concentration which is about equal to or greater than the parent non-flue-cured tobacco plant.

In one embodiment the cured hybrid plant or a part thereof comprises one or more flavour compounds which are a breakdown product of cis-abienol, a concentration of total sucrose esters and a concentration of cis-abienol which is about equal to or greater than the concentration in the cured parent non-flue-cured tobacco plant.

In one embodiment the cured hybrid plant or a part thereof comprises one or more flavour compounds which are a breakdown product of cis-abienol at a concentration which is about equal to or greater than the concentration in the cured parent non-flue-cured tobacco plant and a concentration of total sucrose esters which is about equal to or greater than the concentration of total sucrose esters in the parent non-flue-cured tobacco plant.

In one embodiment the cured hybrid plant or a part thereof comprises one or more flavour compounds which are a breakdown product of cis-abienol at a concentration which is about equal to or greater than the concentration in the cured parent non-flue-cured tobacco plant and a concentration of cis-abienol which is about equal to or greater than the concentration in the cured parent non-flue-cured tobacco plant and a concentration of total sucrose esters which is about equal to or greater than the concentration of total sucrose esters in the parent non-flue-cured tobacco plant.

In one embodiment, "a breakdown product of cis-abienol" may mean one of the following compounds: norambreinolide, (12R, 13R)-8,12-Epoxy-14-labden-13-ol and (12R, 13R)-8,13-Epoxy-14-labden-12-ol.

In one embodiment the breakdown product(s) of cis-abienol may comprise two or more of the following compounds: norambreinolide, (12R, 13R)-8,12-Epoxy-14-labden-13-ol and (12R, 13R)-8,13-Epoxy-14-labden-12-ol.

In one embodiment the breakdown product(s) of cis-abienol may comprise all three of the following compounds: norambreinolide, (12R, 13R)-8,12-Epoxy-14-labden-13-ol and (12R, 13R)-8,13-Epoxy-14-labden-12-ol.

In one embodiment the present hybrid plant or part thereof may further comprise one or more of quinic acid, chlorogenic acid, rutin, β Carotene and Lutein at a concentration which is greater than the concentration in the cured parent non-flue-cured tobacco plant. In one embodiment the present hybrid plant or part thereof may further comprise each of quinic acid, chlorogenic acid, rutin, β Carotene and Lutein at a concentration which is greater than the concentration in the cured parent non-flue-cured tobacco plant.

In one embodiment the cured hybrid plant or a part thereof comprises one or more flavour compounds which are a breakdown product of cis-abienol at a concentration which is about equal to or greater than the concentration in the cured parent non-flue-cured tobacco plant, a concentration of cis-abienol which is about equal to or greater than the concentration in the cured parent non-flue-cured tobacco plant and a concentration of total sucrose esters which is about equal to or greater than the concentration of total sucrose esters in the parent non-flue-cured tobacco plant and further comprises one or more of quinic acid, chlorogenic acid, rutin, β Carotene and Lutein at a concentration which is greater than the concentration in the cured parent non-flue-cured tobacco plant.

In one embodiment the cured hybrid plant or a part thereof comprises one or more flavour compounds which are a breakdown product of cis-abienol at a concentration which is about equal to or greater than the concentration in the cured parent non-flue-cured tobacco plant, a concentration of cis-abienol which is about equal to or greater than the concentration in the cured parent non-flue-cured tobacco plant and a concentration of total sucrose esters which is about equal to or greater than the concentration of total sucrose esters in the parent non-flue-cured tobacco plant and further comprises each of quinic acid, chlorogenic acid, rutin, β Carotene and Lutein at a concentration which is greater than the concentration in the cured parent non-flue-cured tobacco plant.

In one embodiment, the present hybrid plant or a part thereof comprises cis-abienol at a concentration which is about equal to or greater than the concentration of cis-abienol in the parent non-flue-cured tobacco plant, and the hybrid plant further comprises one or more commercially desirable traits selected from the group consisting of drought resistance, pest resistance, mature plant height, harvestable leaf number, average node length, cutter leaf length, cutter leaf width, and yield comparable to those said traits in the flue-cured parent of the hybrid when grown under similar growth conditions.

The cis-abienol concentration in the present hybrid tobacco plant or a part thereof may be between about 2-fold to 20-fold, 2-fold to 15-fold, 2-fold to 10-fold, 2-fold to 8-fold or 4-fold to 8-fold greater than the cis-abienol concentration in the flue-cured parent of the hybrid.

The cis-abienol concentration in the present hybrid tobacco plant or a part thereof may be at least 2-fold, at least 4-fold, at least 8-fold, at least 10-fold, at least 15-fold or at least 20-fold greater than the cis-abienol concentration in the flue-cured parent of the hybrid.

The cis-abienol concentration may be measured in green tobacco (e.g. green tobacco leaves) (e.g. prior to processing (i.e. curing)) or from processed (e.g. cured) tobacco or part thereof (e.g. tobacco leaf).

Sucrose Esters

In one aspect, the present hybrid tobacco plant or part thereof comprises total sucrose esters at a concentration about equal to or greater than the total sucrose ester concentration in the non flue-cured parent of the hybrid and the hybrid plant further comprises one or more commercially desirable traits selected from the group consisting of drought resistance, pest resistance, mature plant height, harvestable leaf number, average node length, cutter leaf length, cutter leaf width, and yield comparable to those said traits in the flue-cured parent of the hybrid when grown under similar growth conditions.

The total sucrose ester concentration in the present hybrid tobacco plant or a part thereof may be between about 2-fold to 20-fold, 2-fold to 15-fold, 2-fold to 10-fold, 2-fold to 8-fold or 4-fold to 8-fold greater than the total sucrose ester concentration in the flue-cured parent of the hybrid.

The total sucrose ester concentration in the present hybrid tobacco plant or a part thereof may be between at least about 2-fold, at least about 4-fold, at least about 8-fold, at least about 15-fold or at least about 20 fold greater than the total sucrose ester concentration in the flue-cured parent of the hybrid.

The sucrose ester concentration may be measured in green tobacco (e.g. green tobacco leaves) (e.g. prior to processing (i.e. curing)) or from processed (e.g. cured) tobacco or part thereof (e.g. tobacco leaf).

In a further aspect, a hybrid tobacco plant or a part thereof of the present invention may comprise total sucrose esters at a concentration of at least about 10, at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190 or at least about 200 mg/cm$^2$.

Concentrations and/or levels of flavour compounds can be measured by any known metabolite profiling method in the art including, without limitation, gas chromatography mass spectrometry (GC-MS), Nuclear Magnetic Resonance Spectroscopy, liquid chromatography-linked mass spectrometry (See The Handbook of Plant Metabolomics, edited by Weckwerth and Kahl, (Wiley-Blackwell); May 28, 2013—which is incorporated herein by reference). Suitably, the concentration and/or level of flavour compound may be determined using liquid chromatography-linked mass spectrometry. Suitably, concentrations and/or levels of flavour compounds can be measured by ultra performance liquid chromatography (UPLC) coupled to a high-resolution mass spectrometry (HRMS) detection system (UPLC-HRMS); or by high-throughput screening (HTS) methodology with flow injection analysis (FIA) coupled to a high-resolution mass spectrometry detection system (HTS-FIA-HRMS). Such methods may be performed, for example, using an ACQUITY I-CLASS UPLC® (Waters®, USA) coupled with high resolution mass spectrometry (SYNAPT G2-Si®, Waters®, USA) mass spectrometer. Suitable methodologies for such analysis are described in the present examples.

Accordingly, concentrations and/or levels of flavour compounds may suitably be measured by extracting powdered cured leaf samples with methanol:water solution plus chloroform to generate an aqueous phase and an organic phase before analysis of the aqueous and/or organic phase by HPLC-HRMS or HTS-FIA-HRMS analysis. Suitable methods for said extraction and analysis are described in the present examples.

The term "tobacco" as used herein refers to a plant in the genus Nicotiana that is used in the production of tobacco products and it is not intended that the term "tobacco" extends to Nicotiana species that are not useful for the production of tobacco products.

A part of a tobacco plant as referred to herein may be selected from selected from the group consisting of a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. Suitably the part of the tobacco plant is an aerial part of the plant, in particular a leaf or a stem. In a preferred embodiment, the part of the plant is a leaf.

As mentioned above, without wishing to be limited by any scientific or biochemical theory, plant genetics can also impact the chemistry profile of the tobacco leaf including the compounds associated with aroma and flavour of a tobacco. Tomita et al. Agric. Biol. Chem., 44 (10):2517-18 (1980) reported that the cis-abienol production in tobacco variety Galpao No. 1 is genetically controlled by a single dominant gene. Analysis of backcross populations and F2 progenies of a cross between a cigar-filler type tobacco, TI 165 and a flue-cured tobacco, NC 2326 suggested that the production of β-methylvaleric acid is controlled by a single dominant gene (see Gwynn et al., Tobacco Science, 15 29:79-81 (1985).

Flue-cured tobacco is the most widely grown tobacco (40% of world tobacco production) and is also known as "Bright" or "Virginia" tobacco. Flue-cured leaf is characterised by a high sugar:nitrogen ratio. This ratio is enhanced by picking the leaf in an advanced stage of ripeness and by the curing process which allows certain chemical changes to occur in the leaf. The leaves are relatively large with the largest at midstalk. A well grown plant will be topped at a height of about 39 to 51 inches with 18-22 harvestable leaves. Yields average around 2200 lbs/acre with some in excess of 3000 lbs/acre. The leaves are harvested as they mature from the ground up.

Flue-curing is well-known in the art and refers to the process of curing tobacco with flues which are fed by fire boxes or gas fuelled systems. This process heat-cures the tobacco without exposing it to smoke, slowly raising the temperature over the course of the curing. This method produces tobacco that is high in sugar and has medium to high levels of nicotine. The Smith Tobacco Barn is an example of a traditional, flue-cured tobacco barn.

The flue-cured tobacco for use (e.g. as a parent tobacco) in the present invention may be a variety of Nicotiana tabacum species. The use of tobacco cultivars and elite tobacco cultivars is also contemplated herein. The tobacco plant (e.g. the flue-cured parent tobacco plant) for use herein may therefore be a tobacco variety or elite tobacco cultivar.

In some embodiments, the flue-cured parent tobacco plant may be, for example, selected from one or more of the following varieties: N. tabacum K 149, N. tabacum K 326, N. tabacum K 346, N. tabacum K 358, N. tabacum K 394, N. tabacum K 399, N. tabacum K 730, N. tabacum McNair 373, N. tabacum NC 2000, N. tabacum PG 01, N. tabacum PG 04, N. tabacum P01, N. tabacum P02, N. tabacum P03, N. tabacum RG 11, N. tabacum RG 17, N. tabacum RG 8, N. tabacum Speight G-28, N. tabacum Kutsage E1, N. tabacum McNair 944, N. tabacum NC 2326, N. tabacum NC 71, and N. tabacum NC 297.

Non-limiting examples of varieties or cultivars are: Coker 176, Coker 319, Coker 371 Gold, Coker 48, K 149, K 326, K 346, K 358, K394, K 399, K 730, McNair 373, McNair 944, NC 291, NC 297, NC 299, OXFORD 207, PD 7302 LC, PD 7309 LC, PVH03. PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight RG 11, RG 8, VA 509, Low converter subvarieties of the above, are also contemplated.

In one aspect, hybrid tobacco plants or seeds of the present invention have a flue-cured parent tobacco plant selected from the group consisting of CSC 07, CC 13, CC 27, CC 33, CC 37, CC 65, CC 67, CC 700, OF 318, GL 338, GL368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. See NC State University, 2013 Guide FLUE-CURED TOBACCO, published by North Carolina Cooperative Extension Service.

Suitably, the hybrid tobacco plants or seeds of the present invention have a CSC 07 flue-cured parent tobacco plant.

In another aspect, hybrid tobacco plants or seeds of the present invention have a flue-cured parent tobacco plant selected from the group consisting of CSC 07, Coker48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1.

In a further aspect, hybrid tobacco plants or seeds of the instant disclosure have a flue-cured parent tobacco plant from the variety K326.

In one aspect, hybrid tobacco plants or seeds have a flue-cured parent tobacco plant which is a hybrid and has at least 50% of its nuclear DNA comes from a flue-cured inbred variety selected from the group consisting of CSC 07, CC 13, CC 27, CC 33, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, and SPEIGHT 236.

In another aspect, the flue-cured parent tobacco plant is a hybrid and has at least 50% of its nuclear DNA comes from a flue-cured inbred variety selected from the group consisting of CSC 07, Coker 48, Coker 176, Coker 371-Gold, Coker 319, Coker 347, GL 939, K 149, K326, K 340, K 346, K 358, K 394, 15 K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, and Va 182.

Non flue-cured tobaccos include air-cured (e.g. Burley, Maryland, dark and Galpão), or fire-cured (e.g. dark)

tobacco types. Accordingly, one parent of the present hybrid tobacco plant may be a non flue-cured parent tobacco selected from a Galpão, Burley, Maryland or dark tobacco plant.

Air-cured tobaccos include Galpão, Burley, Maryland, and dark tobaccos. The common factor is that curing is primarily without artificial sources of heat and humidity. Burley tobaccos are light to dark brown in colour, high in oil, and low in sugar. Burley tobaccos are air-cured in barns. Major Burley growing countries are Argentina, Brazil, Italy, Malawi, and the U.S. Burley tobacco plants include, for example, Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R711, R 712, NCBH 129, Bu 21xKy 10, HBO4P, Ky 14xL 8, Kt 200, Newton 98, Pedigo 561, Pf561 and Va 509.

Maryland tobaccos are extremely fluffy, have good burning properties, low nicotine and a neutral aroma. Major Maryland growing countries include the U.S. and Italy. Maryland tobacco plants include, for example, Md 10, Md 40, Md 201, Md 609, Md 872 and Md 341.

Dark air-cured tobaccos are distinguished from other types primarily by its fermentation process which gives dark air-cured tobacco its medium- to dark-brown colour and distinct aroma. Their leaves have low sugar content but high nicotine content. Dark air-cured tobaccos are mainly used in the production of chewing tobacco and snuff. Major growing regions for dark fire-cured tobaccos are Tennessee, Kentucky, and Virginia, USA.

Dark fire-cured tobacco plants include, for example, Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

Galpão (Galpão Comum) is a specific variety of *Nicotiana tabacum* L characterized by a unique aroma and flavour profile. These characteristics are the result of the unique flavour and aroma compounds or the precursors of these compounds that are present at certain levels in the cured leaf. Major Galpão Comum growing countries include Brazil, Argentina and some other South American countries. Galpão Comum emerged from selections of tobacco originally used by the Central American people. Through selection of the most appropriate varieties emerged a large number of local selections of different types, one of which was Galpão Comum.

Galpão Comum has a particular leaf shape—namely broad leaf which is typically bigger than Burley and Virginia varieties. The yield for a high quality Galpão Comum tobacco is close to 2500 lbs/acre while for Oriental tobacco types the yield is typically in the range of 600 to 1100 lbs/acre. Galpão Comum typically has green leaves and stalk and a plant size which is more similar to Burley and Virginia tobacco than Oriental tobacco. The leaves of Galpão Comum tobaccos are sticky and chemically they are very rich in sucrose esters (β-methyl-valeric sucrose ester) and cis-abienol. The mibribs of a Galpão Comum are stickier than an oriential tobacco type.

In one embodiment the non-flue cured parent tobacco plant has broad leaves which are bigger than the average Burley, Virginia or Oriental varieties.

In another embodiment the non-flue cured parent tobacco plant is taller than Oriental tobacco.

In a further embodiment the non-flue cured parent tobacco has leaves and/or midribs which are sticky.

In some embodiments, the Galpão Comum parent tobacco plant may be, for example, selected from one or more of the following varieties: DT 538 LC Galpao tobacco, *N. tabacum* TI-1068, PALOTINA, CO-D, CO-C and ESPADA. The Galpão Comum plant for use as a parent plant in the present invention may be a Galpão Comum variety.

In a preferred embodiment, the non flue-cured parent of the present hybrid tobacco plant is a *Nicotiana tabacum* L var. Galpão Comum parent tobacco plant.

All foregoing mentioned specific varieties of dark air-cured, Burley, Maryland, dark fire-cured type or Galpão are only listed for exemplary purposes. Any additional dark air-cured, Burley, Maryland, dark fire-cured or Galpão varieties are also contemplated in the instant application. In one embodiment the *Nicotiana tabacum* L var. Galpão Comum parent tobacco plant according to the present invention in one which has a dominant cis-abienol gene.

The non-flue cured parent of the present hybrid is not an Oriental tobacco plant.

In one embodiment the present invention relates to a hybrid plant (e.g. according to the present invention) comprising an introgression from the non flue-cured parent plant, said introgression comprising at least the cis-abienol dominant gene.

A cured hybrid plant or part thereof of the present invention preferably exhibits one or more flavour compounds which are breakdown products of cis-abienol at a concentration higher than in a plant that lacks the introgression. Suitably, the level of one or more cis-abienol breakdown products in the cured hybrid plant or part thereof is increased by at least 5%, suitably by at least 10% or at least 20% or at least 30%, at least 50% or at least 100% compared with a corresponding cured tobacco flue cured breeding line lacking the introgression.

A hybrid plant or part thereof of the present invention preferably exhibits total sucrose esters at a concentration higher than in a plant that lacks the introgression. Suitably, the level of total sucrose esters in the hybrid plant or part thereof is increased by 2-fold to 20-fold, 2-fold to 15-fold, 2-fold to 10-fold, 2-fold to 8-fold or 4-fold to 8-fold compared with a corresponding tobacco flue cured breeding line lacking the introgression.

As used herein, the terms "introgression", "introgressed" and "introgressing" refer to both a natural and artificial process, and the resulting events, whereby genes of one species, variety or cultivar are moved into the genome of another species, variety or cultivar, by crossing those species. The process may optionally be completed by back-crossing to the recurrent parent.

As used herein, a non flue-cured parent plant may be from a non flue-cured inbred variety or a non flue-cured hybrid in which at least 50% of its nuclear DNA comes from one non flue-cured variety. In one aspect, a non flue-cured hybrid which is used as a non flue-cured parent plant herein, can comprise one or more segments of nuclear DNA introgressed from another variety, where greater than about 50%, 60%, 75%, 80%, 85%, 90%, 95%, 97%, or 99% of the nuclear DNA is DNA derived from one single non flue-cured variety.

A flue-cured parent plant for use in the present invention may be from a flue-cured inbred variety or a flue-cured hybrid in which at least 50% of its nuclear DNA comes from one flue-cured variety. In one aspect, a flue-cured hybrid which is used as a flue-cured parent plant herein, can comprise one or more segments of nuclear DNA introgressed from another variety, where greater than about 50%, 60%, 75%, 80%, 85%, 90%, 95%, 97%, or 99% of the nuclear DNA is DNA derived from one single flue-cured variety.

In one aspect, the present invention provides a population of hybrid tobacco plants (or F1 hybrid tobacco plants) according to the present invention. In another aspect, the present invention provides hybrid tobacco seeds (or F1 hybrid tobacco seeds) according to the present invention. In a further aspect, the present invention provides a container of hybrid tobacco seeds (or F1 hybrid tobacco seeds) according to the present invention.

A container of hybrid tobacco seeds of the present invention may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Containers of tobacco seeds may be any container available in the art. By way of non-limiting example, a container may be a box, a bag, a packet, a pouch, a tape roll, a tube, or a bottle.

In one aspect, a population of hybrid tobacco plants of the present invention has a planting density of between about 5,000 and about 8000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre.

A hybrid tobacco plant of the present invention may also comprise one or more traits selected from the group consisting of drought resistance, pest resistance, mature plant height, harvestable leaf number, average node length, cutter leaf length, cutter leaf width, and yield comparable to those one or more traits in flue-cured parent of the hybrid when grown under similar growth conditions.

In one aspect, the mature plant height of a hybrid tobacco plant according to the present invention is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, between 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the mature plant height of the flue-cured parent of the hybrid, when grown in similar field conditions.

In one aspect, the mature plant height of a hybrid tobacco plant according to the present invention is between about 30 and about 65 inches, between about 32.5 and about 62.5 inches, between about 35 and about 60 inches, between about 37.5 and about 57.5 inches, 15 between about 40 and about 55 inches, between about 42.5 and about 52.5 inches, and between about 45 and about 50 inches.

In another aspect, the mature plant height of a hybrid tobacco plant according to the present invention is between about 30 and about 100 inches, between about 32.5 and about 100 inches, between about 35 and about 100 inches, between about 37.5 and about 100 inches, 20 between about 40 and about 100 inches, between about 42.5 and about 100 inches, between about 45 and about 100 inches, between about 47.5 and about 100 inches, between about 50 and about 100 inches, between about 52.5 and about 100 inches, between about 55 and about 100 inches, between about 65 and about 100 inches, between about 67.5 and about 100 inches, between about 70 and about 100 inches, between about 72.5 and about 100 inches, between 25 about 75 and about 100 inches, between 77.5 and about 100 inches, between about 80 and about 100 inches, between about 82.5 and about 100 inches, between about 85 and about 100 inches, between about 87.5 and about 100 inches, between about 90 and about 100 inches, between about 92.5 and about 100 inches, between about 95 and about 100 inches, and between about 97.5 and about 100 inches.

Mature plant height of a hybrid tobacco plant mentioned herein is measured from a plant without topping. In one aspect, a hybrid tobacco plant of the present invention is grown and harvested without topping.

In one aspect, a hybrid tobacco plant of the present invention comprises at maturation a similar number of harvestable leaves compared to the flue-cured parent of the hybrid when grown in similar field conditions.

In one aspect, the number of harvestable leaves in a hybrid tobacco plant of the present invention is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the number of harvestable leaves in the non flue-cured parent or the flue-cured parent of the hybrid when grown in similar field conditions.

Unless specified otherwise, used herein, tobacco yield refers to cured leaf yield which is calculated based on the weight of cured tobacco leaves per acre under standard field conditions following standard agronomic and curing practice.

In one aspect, a hybrid tobacco plant of the present invention has a yield between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the yield of the flue-cured parent of the hybrid when grown in similar field conditions.

In another aspect, the yield of a hybrid tobacco plant of the present invention is approximately 1.5, 1.6, 1.7, 1.8, 1.9, 2.0, 2.1, 2.2, 2.3, 2.4, 2.5, 2.6, 2.7, 2.8, 2.9, or 3.0 times of the yield of the non-flue cured parent of the hybrid when grown in similar field conditions.

In another aspect, the yield of a hybrid tobacco plant of the present invention is comparable to the yield of the flue cured parent of the hybrid when grown in similar field conditions.

In one aspect, a hybrid tobacco plant of the present invention provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre.

In another aspect, a hybrid tobacco plant of the present invention provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre.

In a further aspect, a hybrid tobacco plant of the present invention provides a yield selected from the group consisting of about between 1200 and 3500, between 1200 and 3400, between 1200 and 3300, between 1200 and 3200, between 1200 and 3100, between 1200 and 3000, between 1200 and 2900, between 1200 and 2800, between 1200 and 2700, between 1200 and 2600, between 1200 and 2500, between 1200 and 2400, between 1200 and 2300, between 1200 and 2200, between 1200 and 2100, between 1200 and 2000, between 1200 and 1900, between 1200 and 1800, between 1200 and 1700, between 1200 and 1600, between 1200 and 1500, and between 1200 and 1400 lbs/acre.

In one aspect, a hybrid tobacco plant of the present invention provides cured tobacco of commercially acceptable grade. In one embodiment, a hybrid tobacco plant of the present invention provides flue-cured tobacco of commercially acceptable grade.

Tobacco grades are evaluated based on factors including, but not limited to, the leaf stalk position, leaf size, leaf colour, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast.

In one aspect, a hybrid tobacco plant of the present invention is male sterile. In another aspect, a hybrid tobacco plant of the present invention is cytoplasmic male sterile. Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development Crop Species. W. H. Fehr (ed.), MacMillan Publishing Go., Inc., New York, N.Y. 761 pp.

Either parent of a hybrid can be male sterile or cytoplasmic male sterile.

In one aspect, a hybrid plant of the present invention may comprise a trichome density similar to their corresponding non flue-cured parent. In another aspect, a hybrid plant of the present invention comprises a trichome density comparable to their corresponding non flue-cured parent.

In a further aspect, the trichome density of a hybrid according to the present invention is about between 95% to 105%, between 90% and 110%, between 85% and 115%, between 80% and 120%, between 75% and 125%, between 70% and 130%, between 65% and 135%, between 60% and 140%, or between 55% and 145% of the trichome density in a leaf of a comparable stock position from their corresponding non flue-cured parent.

Trichome densities can be measured by counting the number of trichomes per unit leaf area.

In one aspect, a hybrid tobacco plant of the present invention is adapted for machine harvesting. In another aspect, a hybrid tobacco plant of the present invention may be harvested mechanically.

In another aspect, the cured hybrid tobacco plant or part thereof of the present invention comprises one or more flavour compounds which are a breakdown product of cis-abienol at a concentration which is about equal to or greater than the concentration in the parent non-flue-cured tobacco plant, and the hybrid tobacco plant further provides a yield between 60% and 100%, between 80% and 100%, or between 90% and 100% of the yield of the flue-cured parent of the hybrid when grown in similar field conditions.

In another aspect, the cured hybrid tobacco plant or part thereof comprises one or more flavour compounds which are a breakdown product of cis-abienol at a concentration which is about equal to or greater than the concentration in the parent non-flue-cured tobacco plant, and the hybrid tobacco plant further comprises a yield approximately 1.6, 1.8, 2.0, 2.2, or 2.4 times of the yield of the flue-cured parent of the hybrid when grown in similar field conditions.

In another aspect, the hybrid comprises a concentration of total sucrose esters which is about equal to or greater than the concentration of total sucrose esters in the non flue-cured parent of the hybrid when grown under similar conditions, and further provides a yield between 60% and 100%, between 80% and 100%, or between 90% and 100% of the yield of the flue-cured parent of the hybrid when grown in similar field conditions.

In another aspect, the hybrid comprises a concentration of total sucrose esters which is about equal to or greater than the concentration of total sucrose esters in the non flue-cured parent of the hybrid, and further provides a yield approximately 1.6, 1.8, 2.0, 2.2, or 2.4 times of the yield of the flue-cured parent of the hybrid when grown in similar field conditions.

Hybrids can be produced by preventing self-pollination of female parent plants (i.e., seed parents) of a first variety, permitting pollen from male parent plants of a second variety to fertilize the female parent plants, and allowing hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility wherein a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting F1 seed is harvested.

In one aspect, the foregoing female parents are male sterile. In another aspect, the foregoing female parents are cytoplasmic male sterile.

Plants can be used to form single-cross tobacco F1 hybrids. Pollen from a male parent plant is manually transferred to an emasculated female parent plant or a female parent plant that is male sterile to form F1 seed. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed. Self-incompatibility can be used to particular advantage to prevent self-pollination of female parents when forming a double-cross hybrid.

The instant disclosure provides a method of producing an F1 hybrid, comprising crossing a flue-cured parent tobacco plant with a non-flue-cured parent tobacco plant and selecting an F1 hybrid.

In one aspect, when cured, the selected F1 hybrid comprises one or more flavour compounds which are a breakdown product of cis-abienol at a concentration which is similar to or greater than the concentration in the parent non-flue-cured tobacco plant.

In one aspect, the selected F1 hybrid comprises a total sucrose ester concentration which is similar to or greater than the concentration of total sucrose esters in the parent non-flue-cured tobacco plant.

The present invention also provides a method of growing an F1 hybrid plant of the present invention, where the method comprising planting an F1 hybrid seed according to the present invention and harvesting tobacco material (e.g. tobacco leaf) from said F1 hybrid plant.

The instant disclosure also provides for breeding and progenies of an F1 hybrid tobacco plant disclosed herein. Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in a F2 or backcross generation using F1 hybrid plants disclosed herein or further crossing the F1 hybrid plants with other donor plants with an agronomically desirable genotype. Plants in the F2 or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. A recurrent parent in the instant disclosure can be a flue-cured variety or a non flue-cured variety. Other breeding techniques can be found, for example, in Wernsman, E. A., and Rufty, R. C. 1987. Chapter Seventeen. Tobacco Pages 669-698 In: Cultivar Development. Crop Species. W. H. Fehr (ed.), MacMillan Publishing Go., Inc., New York, N.Y., incorporated herein by reference in their entirety.

This disclosure also includes, without limitation, breeding with other *Nicotiana* species than *Nicotiana tabacum*. Such *Nicotiana* species which exhibit breeding compatibility with *Nicotiana tabacum* include, without limitation, *Nicotiana amplexicaulis*, PI 271989; *Nicotiana benthamiana* PI 555478; *Nicotiana bigelovii* PI 555485; *Nicotiana debneyi; Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica; Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572. See also, Compendium of Tobacco Diseases published by American Phytopathology Society, or The Genus *Nicotiana* Illustrated, published by Japan Tobacco Inc, hereby incorporated by reference in their entirety.

Results of a plant breeding program using the tobacco plants described herein includes useful lines, cultivars, varieties, progeny, inbreds, and hybrids of the present invention. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation.

A "line" as distinguished from a variety most often denotes a group of plants used non-commercially, for example in plant research. A line typically displays little overall variation between individuals for one or more traits of interest, although there may be some variation between individuals for other traits.

An additional aspect of the instant disclosure provides a method for producing a tobacco plant that contains in its nuclear DNA one or more transgenes, comprising crossing a plant disclosed in the instant disclosure with a second plant containing one or more transgenes wherein progeny are produced, so that the nuclear DNA of the progeny that result from the cross comprise the transgene(s) optionally operably linked to one or more regulatory elements.

The instant disclosure further provides for the vegetative propagation of a plant disclosed herein. In one aspect, the instant disclosure provides for a method of vegetatively propagating a plant of a tobacco cultivar comprising collecting tissue capable of being propagated, cultivating the tissue to obtain a proliferated shoot and rooting the proliferated shoots to obtain a rooted plantlet.

A plant disclosed herein may be further bred by mutagenesis followed by selecting or screening the mutagenized plant material, or progeny thereof. Such screening and selection methodologies are known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

It is understood that any tobacco plant of the present invention may be transformed by a genetic construct or transgene using a technique known in the art.

Any plant of the present invention can be used as a basis for tissue culture, transformed, or a combination of any of these. In an aspect, a plant of the instant disclosure derived by tissue culture, transformation, or both has essentially all of the morphological and physiological characteristics of initial cultivar.

The present invention further provides a method for screening a hybrid made between a parent flue-cured tobacco plant and a parent non-flue-cured tobacco plant as described herein, which comprises the step of determining the level of a breakdown product(s) of cis-abienol in the cured hybrid or a part thereof and/or the total concentration of sucrose esters in the hybrid. The method may further comprise the step of selecting a hybrid which, when cured, has one or more flavour compounds which are a breakdown product of cis-abienol at a concentration which is similar to or greater than the concentration in the parent non-flue-cured tobacco plant and/or which hybrid has a total concentration of sucrose esters which is about equal to or greater than the total concentration of sucrose esters in the parent non-flue-cured tobacco plant.

The present invention provides cured tobacco material, tobacco blends, and tobacco products made from tobacco plants of the present invention. In one aspect, the cured tobacco material of the instant disclosure is flue-cured.

Tobacco material obtained from the tobacco lines, varieties or hybrids of the instant disclosure can be used to make tobacco products including, without limitation, cigarette products (e.g., cigarettes and bidi cigarettes), cigar products (e.g., cigar wrapping tobacco and cigarillos), pipe tobacco products, products derived from tobacco, tobacco derived nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, and the like.

Tobacco products derived from plants of the present invention also include cigarettes and other smoking articles, particularly those smoking articles including filter elements, wherein the rod of smokable material includes cured tobacco within a tobacco blend. In an aspect, a tobacco product of the instant disclosure is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the instant disclosure is a smokeless tobacco product.

In a further aspect, a tobacco product of the instant disclosure is selected from the group consisting of loose leaf chewing tobacco, plug chewing tobacco, moist snuff, and nasal snuff.

In yet another aspect, a tobacco product of the instant disclosure is selected from the group consisting of an electronically heated cigarette, an e-cigarette, an electronic vaporing device.

In an aspect, a tobacco product of the instant disclosure can be a blended tobacco product. In another aspect, a tobacco product of the instant disclosure can be a low nicotine tobacco product. In a further aspect, a tobacco product of the instant disclosure may comprise nornicotine at a level of less than about 3 mg/g. For example, the nornicotine content in such a product can be 3.0 mg/g, 2.5 mg/g, 2.0 mg/g, 1.5 mg/g, 1.0 mg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable.

In one aspect, a tobacco blend product of the instant disclosure comprises at least about 5, 10, 20, 30, 40, 50, 60, 70, 80, 90, or 95 percent by dry weight of tobacco cured from a hybrid plant of the present invention.

In another aspect, a tobacco blend product of the present invention comprises by dry weight tobacco material prepared from hybrid plants of the present invention at a ratio between 25% and 30%, between 25% and 35%, between 25% and 40%, between 25% and 45%, between 25% and 50%, between 30% and 45%, between 35% and 40%, between 30% and 50%, between 35% and 50%, between 45% and 50%, or between 45% and 50%.

The instant disclosure further provides a method manufacturing a tobacco product, where the method comprising conditioning aged tobacco material made from a hybrid tobacco plant of the present invention to increase its moisture content from between about 12.5% and about 13.5% to about 21%, blending the conditioned tobacco material to produce a desirable blend.

In one embodiment the plant propagation material may be obtainable (e.g. obtained) from a tobacco plant of the invention.

A "plant propagation material" as used herein refers to any plant matter taken from a plant from which further plants may be produced. Suitably the plant propagation material may be a seed.

In one embodiment the tobacco cell, tobacco plant and/or plant propagation material may be obtainable (e.g. obtained) by a method according to the invention.

In one embodiment the tobacco plant in accordance with the present invention comprises a tobacco cell of the invention.

In one embodiment there is provided the use of a tobacco cell as provided for in the foregoing embodiments for production of a tobacco product. Additionally there is provided the use of a hybrid tobacco plant as described herein to breed a tobacco plant.

The present invention also provides in another embodiment the use of a tobacco plant according to the present invention for the production of a tobacco product. In another embodiment there is provided the use of a hybrid tobacco plant of the invention to grow a crop.

Commercially Desirable Traits

The term "commercially desirable traits" will include traits such as yield, mature plant height, harvestable leaf number, average node length, cutter leaf length, cutter leaf width, quality, abiotic (for instance drought) stress tolerance, herbicide tolerance and/or biotic (for instance insect, bacteria or fungus) stress tolerance.

Plant Breeding

In one embodiment the present invention provides a method for the production of a hybrid plant of the present invention, comprising:
- a) crossing a donor non-flue cured plant having one or more flavour compounds as described herein with a recipient flue-cured plant (suitably that does not have said one or more flavour compounds as described herein) which possesses commercially desirable traits;
- b) collecting the seeds resulting from the cross in step a);
- c) regenerating the seeds into plants;
- d) providing one or more backcross generations by crossing the plants of step c) or (optionally selfed) offspring thereof with one or more plants of said recipient flue-cured line to provide backcross plants;
- e) selfing plants of step d) and growing the selfed seed into plants;
- f) optionally repeating said steps of backcrossing and selfing of steps d) and/or e);
- g) identifying and selecting plants from the plants grown in step c), e) or f) having one or more flavour compounds as described herein.

In one embodiment of said method, the step of identification and selection of step g) is performed by marker-assisted selection. The plant obtained following step a) or identified and selected in step g) may be referred to herein as the hybrid plant according to the present invention.

In one embodiment the present invention provides a method of producing a hybrid plant comprising one or more flavour compounds as described herein at a concentration comparable to the concentration of said one or more flavour compounds as described herein in the non flue-cured parent of the hybrid, comprising:
- a. crossing a donor non flue-cured plant having one or more flavour compounds as described herein with a recipient flue-cured plant (suitably that does not have said one or more flavour compounds as described herein) which possesses commercially desirable traits;
- b. isolating genetic material from a progeny of said donor plant crossed with said recipient plant; and
- c. performing molecular marker-assisted selection with a molecular marker comprising:
  - i. identifying an introgressed region comprising at least the cis-abienol dominant gene.

The molecular marker assisted selection may comprise performing PCR to identify an introgressed nucleic acid sequence comprising at least the cis-abienol dominant gene.

In one embodiment the hybrid plant according to the present invention may be a recombinant plant.

The present invention provides a plant obtained (or obtainable) by a method of the present invention.

Products

The present invention also provides for products obtainable or obtained from or comprising tobacco according to the present invention.

In one embodiment there is provided the use of a hybrid tobacco plant of the invention to produce a tobacco leaf. Suitably the tobacco leaf may be subjected to downstream applications such as processing. Thus in one embodiment the use of the foregoing embodiment may provide a processed tobacco leaf. Suitably the tobacco leaf may be subjected to curing, fermenting, pasteurising or combinations thereof.

In another embodiment the tobacco leaf may be cut. In some embodiments the tobacco leaf may be cut before or after being subjected to curing, fermenting, pasteurising or combinations thereof.

In one embodiment the present invention provides a harvested leaf of a hybrid tobacco plant of the invention. In a further embodiment the harvested leaf may be obtainable (e.g. obtained) from a tobacco plant propagated from a propagation material of the present invention. In another embodiment there is provided a harvested leaf obtainable from a method or use of the present invention.

Suitably the harvested leaf may be a cut harvested leaf.

In some embodiments the harvested leaf may comprise viable tobacco cells. In other embodiments the harvested leaf may be subjected to further processing.

There is also provided a processed tobacco leaf. The processed tobacco leaf may be obtainable from a tobacco plant of the invention. Suitably the processed tobacco leaf may be obtainable from a tobacco plant obtained in accordance with any of the methods and/or uses of the present invention. In another embodiment the processed tobacco leaf may be obtainable from a tobacco plant propagated form a tobacco plant propagation material according to the present invention.

The processed tobacco leaf of the present invention may be obtainable by processing a harvested leaf of the invention.

The term "processed tobacco leaf" as used herein refers to a tobacco leaf that has undergone one or more processing steps to which tobacco is subjected to in the art. A "processed tobacco leaf" comprises no or substantially no viable cells.

The term "viable cells" refers to cells which are able to grow and/or are metabolically active. Thus, if a cell is said to not be viable, also referred to as "non-viable" then a cell does not display the characteristics of a viable cell.

The term "substantially no viable cells" means that less than about 5% of the total cells are viable. Preferably, less than about 3%, more preferably less than about 1%, even more preferably less than about 0.1% of the total cells are viable.

In one embodiment the processed tobacco leaf may be processed by one or more of: curing, fermenting and/or pasteurising. Suitably the processed tobacco leaf may be processed by curing.

Tobacco leaf may be cured by any method known in the art. In one embodiment tobacco leaf may be cured by one or more of the curing methods selected from the group consisting of: flue curing, air curing, fire curing and sun curing.

Suitably the tobacco leaf may be air cured. Typically air curing is achieved by hanging tobacco leaf in well-ventilated bars and allowing to dry. This is usually carried out over a period of four to eight weeks. Air curing is especially suitable for burley tobacco.

Suitably the tobacco leaf may be fire cured. Fire curing is typically achieved by hanging tobacco leaf in large barns where fires of hardwoods are kept on continuous or intermittent low smoulder and usually takes between three days and ten weeks, depending on the process and the tobacco.

Preferably, the tobacco leaf may be flue cured. Flue curing may comprise stringing tobacco leaves onto tobacco sticks and hanging them from tier-poles in curing barns. The barns usually have a flue which runs from externally fed fire boxes. Typically this results in tobacco that has been heat-cured without being exposed to smoke. Usually the temperature will be raised slowly over the course of the curing with the whole process taking approximately 1 week.

Suitably the processed tobacco leaf may be processed by fermenting.

Fermentation can be carried out in any manner known in the art. Typically during fermentation, the tobacco leaves are piled into stacks (a bulk) of cured tobacco covered in e.g. burlap to retain moisture. The combination of the remaining water inside the leaf and the weight of the tobacco generates a natural heat which ripens the tobacco. The temperature in the centre of the bulk is monitored daily. In some methods every week, the entire bulk is opened. The leaves are then removed to be shaken and moistened and the bulk is rotated so that the inside leaves go outside and the bottom leaves are placed on the top of the bulk. This ensures even fermentation throughout the bulk. The additional moisture on the leaves, plus the actual rotation of the leaves themselves, generates heat, releasing the tobacco's natural ammonia and reducing nicotine, while also deepening the colour and improving the tobacco's aroma. Typically the fermentation process continues for up to 6 months, depending on the variety of tobacco, stalk position on the leaf, thickness and intended use of leaf.

Suitably the processed tobacco leaf may be processed by pasteurising. Pasteurising may be particularly preferred when the tobacco leaf will be used to make a smokeless tobacco product, most preferably snus.

Tobacco leaf pasteurisation may be carried out by any method known in the art. For example pasteurisation may be carried out as detailed in J Foulds, L Ramstrom, M Burke, K Fagerstrom. Effect of smokeless tobacco (snus) on smoking and public health in Sweden. Tobacco Control (2003) 12: 349-359, the teaching of which is incorporated herein by reference.

During the production of snus pasteurisation is typically carried out by a process in which the tobacco is heat treated with steam for 24-36 hours (reaching temperatures of approximately 100° C.). This results in an almost sterile product and without wishing to be bound by theory one of the consequences of this is believed to be a limitation of further TSNA formation.

In one embodiment the pasteurisation may be steam pasteurisation.

In some embodiments the processed tobacco leaf may be cut. The processed tobacco leaf may be cut before or after processing. Suitably, the processed tobacco leaf may be cut after processing.

In some embodiments the tobacco plant, harvested leaf of a tobacco plant and/or processed tobacco leaf may be used to extract nicotine. The extraction of nicotine can be achieved using any method known in the art. For example a method for extracting nicotine from tobacco is taught in U.S. Pat. No. 2,162,738 which is incorporated herein by reference.

In another aspect the present invention provides a tobacco product.

In one embodiment the tobacco product may be prepared from a tobacco plant of the invention or a part thereof. Suitably the tobacco plant or part thereof may be propagated from a tobacco plant propagation material according to the present invention.

The term "part thereof" as used herein in the context of a tobacco plant refers to a portion of the tobacco plant. Preferably the "part thereof" is a leaf of a tobacco plant.

In another embodiment the tobacco product may be prepared from a harvested leaf of the invention. In a further embodiment the tobacco product may be prepared from a processed tobacco leaf of the invention. Suitably the tobacco product may be prepared from a tobacco leaf processed by one or more of: curing, fermenting and/or pasteurising. Suitably the tobacco product may comprise a cut tobacco leaf, optionally processed as per the foregoing embodiment.

In one embodiment the tobacco product may be a smoking article. As used herein, the term "smoking article" can include smokeable products, such as rolling tobacco, cigarettes, cigars and cigarillos whether based on tobacco, tobacco derivatives, expanded tobacco, reconstituted tobacco or tobacco substitutes.

In another embodiment the tobacco product may be a smokeless tobacco product. The term "smokeless tobacco product" as used herein refers to a tobacco product that is not intended to be smoked and/or subjected to combustion. In one embodiment a smokeless tobacco product may include snus, snuff, chewing tobacco or the like.

In a further embodiment the tobacco product may be a tobacco heating device.

Typically in heated smoking articles, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user.

Aerosol-generating articles and devices for consuming or smoking tobacco heating devices are known in the art. They can include, for example, electrically heated aerosol-generating devices in which an aerosol is generated by the transfer of heat from one or more electrical heating elements of the aerosol-generating device to the aerosol-forming substrate of a tobacco heating device. Suitably the tobacco heating device may be an aerosol-generating device.

Preferably the tobacco heating device may be a heat-not-burn device. Heat-not-burn devices are known in the art and release compounds by heating, but not burning, tobacco. An example of a suitable, heat-not-burn device may be one taught in WO2013/034459 or GB2515502 which are incorporated herein by reference.

In one embodiment the aerosol-forming substrate of a tobacco heating device may be a tobacco product in accordance with the present invention.

Advantages

There are many advantages of the present invention, including one or more of the following advantages:
Taste/flavour benefits: as the present hybrid tobacco provides the flavour characteristics of the non-flue cured parent whilst being produced and cured under similar conditions to the flue-cured parent;
Vegetative vigor: Yield and vegetative vigor are comparable to the commercial flue-cured parent, thus, higher than the corresponding non-flue cured parent.

One potential application for the hybrid according to the present invention is production in countries where importing non flue-cured tobacco is either not allowed by local legislations or expensive. Another possible application is to improve the usage of current Virginia flue-curing barns by using these to cure the present hybrid tobacco alongside typical flue-cured tobacco.

Definitions

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). "Crossing" therefore generally refers to the fertilization of ovules of one individual with pollen from another individual, whereas "selfing" refers to the fertilization of ovules of an individual with pollen from the same individual. When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from said cell and their fusion in fertilization will result in an introgression event.

The term "recipient", as used herein, refers to the plant or plant line receiving the trait, introgression or genomic segment from a donor, and which recipient may or may not have the trait, introgression or genomic segment itself either heterozygous or homozygous.

The term "breeding line", as used herein, refers to a line of a cultivated tobacco (suitably flue-cured tobacco) having commercially valuable or agronomically desirable traits, as opposed to wild varieties. In particular, the breeding line is characterized by having an good yield and/or is preferably resistant to tobacco viruses and/or nematodes and/or other diseases. The term includes reference to elite breeding line or elite line, which represents an essentially homozygous, e.g. inbred or doubled haploid, line of plants used to produce F1 hybrids.

As used herein, the term "hybrid" means any offspring of a cross between two genetically unlike individuals, more preferably the term refers to the cross between two (elite) breeding lines which will not reproduce true to the parent from seed.

The term "donor", as used herein, refers to the non flue-cured plant or plant line from which the trait, introgression or genomic segment originates, and which donor may have the trait, introgression or genomic segment itself either heterozygous or homozygous.

The term "seed" as used herein includes all tissues which result from the development of a fertilized plant egg; thus, it includes a matured ovule containing an embryo and stored nutrients, as well as the integument or integuments differentiated as the protective seed coat, or testa. The nutrients in seed tissues may be stored in the endosperm or in the body of the embryo, notably in the cotyledons, or both.

The term "regenerating", as used herein, with reference to a tobacco plant refers to the formation of a plant that includes a rooted shoot.

The term "backcross", as used herein, refers to the crossing an F1 hybrid with one of the original parents. Typically backcrossing is used to maintain the identity of one parent (species) and to incorporate a particular trait from a second parent (species). The best strategy is to cross the F1 hybrid back to the parent possessing the most commercially desirable traits. Two or more generations of backcrossing may be necessary, but this is practical only if the desired characteristic or trait is present in the F1.

The term "backcross generation", as used herein, refers to the offspring of a backcrossing.

The term "selfed", as used herein, means self-pollinated and includes the fertilization process wherein both the ovule and pollen are from the same plant or plant line.

The term "offspring", as used herein, refers to any progeny generation resulting from a crossing or selfing.

The term "growing", as used herein, refers to the growth of a plant, a process wherein the plant biomass is increased and which coincides with a progressive development of the plant.

The term "identifying", as used herein, refers to a process of establishing the identity or distinguishing character of a plant, such as exhibiting a certain trait.

The term "selecting", as used herein, refers to a process of picking out a certain individual from a group of individuals, usually based on a certain identity of that individual.

The term "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The term "marker", as used herein, refers to refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of the markers described herein which defines a specific genetic and chromosomal location.

The term "gene", as used herein, refers to a hereditary unit consisting of a sequence of DNA that occupies a specific location on a chromosome and that contains the genetic instruction for a particular characteristics or trait in an organism. The term "gene" thus refers to a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (for example, enzymatic activity, ligand binding, signal transduction, etc.) of the polypeptide are retained. The term "gene" encompasses both cDNA and genomic forms of a gene.

The term "recombinant", as used herein with reference to a plant refers to a plant carrying a foreign (donor) gene combined, in whole or in part, in recipient genome.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a protein" or "a nucleic acid sequence" includes a plurality of such candidate agents and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The invention will now be described, by way of example only, with reference to the following Figures and Examples.

EXAMPLES

Example 1—Determination of Flavour Compounds in a Range of Tobacco Types and Hybrid Tobaccos Materials and Methods
Extraction Procedure Aliquots of powdered cured leaf samples (200±5 mg) were transferred to centrifuge tubes of 15 mL and extracted with 5 mL of methanol:water solution (1:1, v/v; aqueous phase) plus 5 mL of chloroform (organic phase) at sonication for 15 min followed by shaking at 250 rpm for 15 min. After, centrifugation was performed at 2,500 rpm for 5 min. Aliquots of 2 mL of aqueous phase (upper layer) and organic phase (lower layer), were filtered throughout 0.22 µm filter (Millipore®, USA), diluted in acetonitrile (20 times) and transferred to vial for high-throughput screening (HTS) with flow injection analysis (FIA) coupled to a high-resolution mass spectrometry detection system (HTS-FIA-HRMS) analysis.

HTS-FIA-HRMS Analysis

All analyses were performed by ACQUITY I-CLASS UPLC® (Waters®, USA) coupled with high resolution mass spectrometry (SYNAPT G2-Si®, Waters®, USA) mass spectrometer. Before each analysis batch was performed a suitable system check (detector setup and mass calibration). The leucine encephalin solution (1 µg/mL) was used for lock mass correction. Nitrogen was used as nebulizer, cone, and desolvation gas. The samples were injected in a continuous stream of mobile phase (Water:Acetonitrile solution 50:50 (v/v) containing 0.1% (v/v) of formic acid) following to the electrospray interface (ESI) at flow rate of 100 µL/min. Both aqueous phase and organic phase were analysed in the both $ESI^-$ and $ESI^+$.

UPLC-HRMS Analysis

All analyses were performed at ACQUITY I-CLASS UPLC® (Waters®, USA) coupled with high resolution mass spectrometry (SYNAPT G2-Si®, Waters®, USA) mass spectrometer. Before each analysis batch was performed a suitable system check (detector setup and mass calibration). The leucine encephalin solution (1 µg/mL) was used for lock mass correction. The data acquisition was performed at positive $MS^E$ resolution mode. The $MS^E$ mode allows obtain the low energy spectrum (MS spectrum) and high energy spectrum (similar to MS/MS spectrum) from a same run without discrimination or ion pre-selection. Nitrogen was used as nebulizer, cone and desolvation gas while argon was used as collision gas. In the reverse-phase UPLC® system, an ACQUITY UPLC® HSS T3 column (2.7×100 mm, 1.8 µm) was used as stationary phase. The mobile phase was composed by water containing 0.1% (v/v) of formic acid (A) and acetonitrile containing 0.1% (v/v) of formic acid (B) in linear gradient elution mode as followed: 1.0 min—50% (A) and 50% (B); 12.0 min—5% (A) and 95% (B); 13.0 min—5% (A) and 95% (B); 13.1 min—50% (A) and 50% (B); 15.0 min—Stop. The mobile flow rate (400 µL/min) and temperature (45° C.) were keep constant throughout the analysis. Only the organic phase was analysed in ESI for the putative identification of chemical markers.

Results

Chemical Evaluation of a Range of Tobacco Types and Hybrid Tobaccos

A chemical analysis of a range of tobacco types (a total of about 772 samples) was performed using a high-throughput screening (HTS) methodology with flow injection analysis (FIA) coupled to a high-resolution mass spectrometry detection system (HTS-FIA-HRMS).

The tobacco types analysed were a Virginia flue-cured tobacco, Oriental sun-cured tobacco, Galpao air-cured tobacco and a hybrid flue-cured tobacco (labelled CSC4901) which hybrid was made from a flue-cured tobacco parent crossed with a Galpao parent.

In other words the flue-cured tobacco parent is a Virginia flue-cured tobacco. The non-flue cured tobacco parent for the hybrid is designated Galpao and is a Nicotiana tabacum L var. Galpão Comum tobacco.

FIG. 1 shows the distribution of the scores obtained from chemical analysis of Galpao, Virginia, Oriental and CSC 4901.

The central distribution of CSC 4901 scores indicates their hybrid chemical characteristics derived from Galpao and Virginia zones. Moreover, the migration of CSC 4901 scores toward the Oriental zone also suggest the introduction of aromatic characteristics in the hybrid (CSC 4901).

Analysis of the Chemical Markers of a Hybrid Tobacco Plant from a Flue-Cured Parent Plant and an Air-Cured Parent Plant A detailed study was performed in order to evaluate the chemical markers that define CSC 4901 hybrid tobacco. A chromatographic technique (UPLC—ultra performance liquid chromatography) coupled to a high-resolution mass spectrometry (HRMS) detection system was used for this purpose and the results acquired are described below.

A comparison between a hybrid plant in accordance with the present invention, namely CSC 4901 and a Virginia flue-cured tobacco plant (namely one of the parental lines used in forming the hybrid plant) was carried out.

Figure 2:
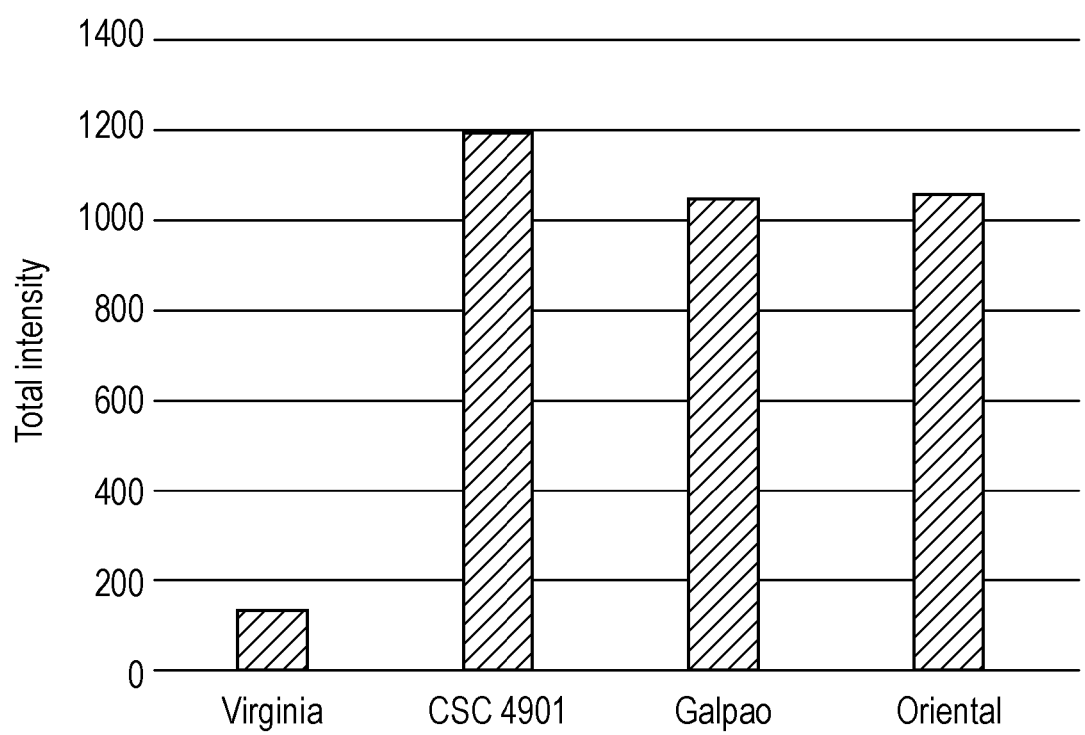
FIG. 2 illustrates the distribution of total sucrose esters obtained from the sum of their individual components in different tobacco types: Galpão, Virginia, Oriental and CSC 4901.

As shown in the FIG. 2, the CSC 4901 shows a high content of sucrose esters when compared to Virginia, but similar to that in Galpao and Oriental.

Figure 3:
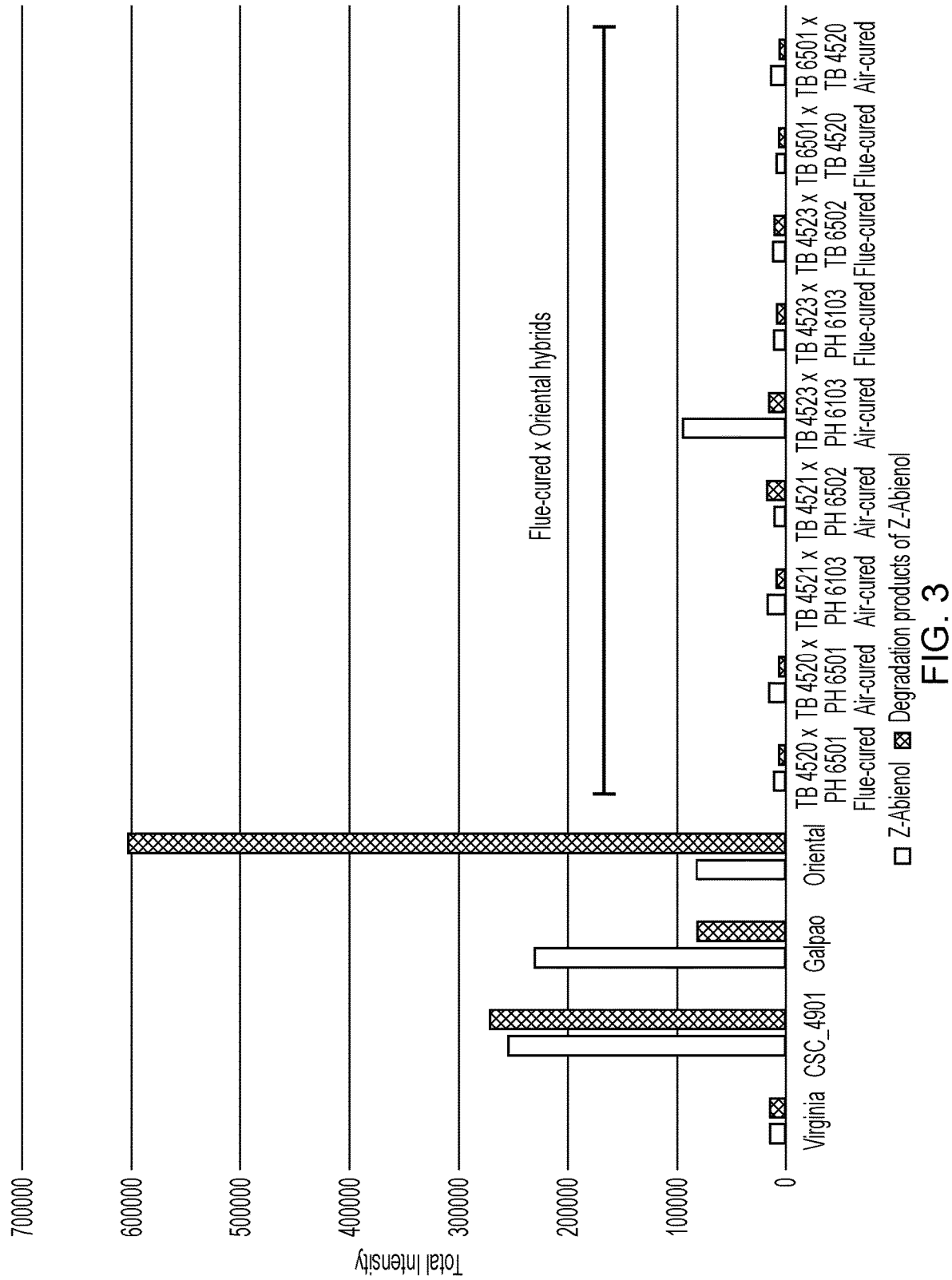
FIG. 3 illustrates the distribution of Z-Abienol and its degradation products in different tobacco types: Galpão, Virginia, Oriental and CSC 4901.

Other important chemical difference introduced from the Galpao parent in the hybrid (CSC 4901) is related to the distribution of diterpene compounds, in particular, Z-Abienol and their degradation products, such as Norambreinolide (Sclareolide), (12R, 13R)-8,12-Epoxy-14-labden-13-ol and (12R, 13R)-8,13-Epoxy-14-labden-12-ol. FIG. 3 illustrates that Z-Abienol content found in CSC 4901 is similar, and in fact higher, than that present in Galpao, but significantly higher than that in Virginia.

The quantification of cis-abienol and its breakdown products was performed by UPLC-HRMS using the same analysis conditions described in the Materials and Methods. The concentration for each of the cis-abienol breakdown products is in FIG. 10. The values represent the mean of target determination obtained from three independent samples for each tobacco type: Virginia, CSC_4901, Galpão and Oriental. The results were expressed in ppm (parts per million), equivalent to µg per g of tobacco in wet basis. Of note, the content of cis-abienol breakdown products for the Virginia parent was lower than detection limit of method (1.5 ppm).

Figure 4:
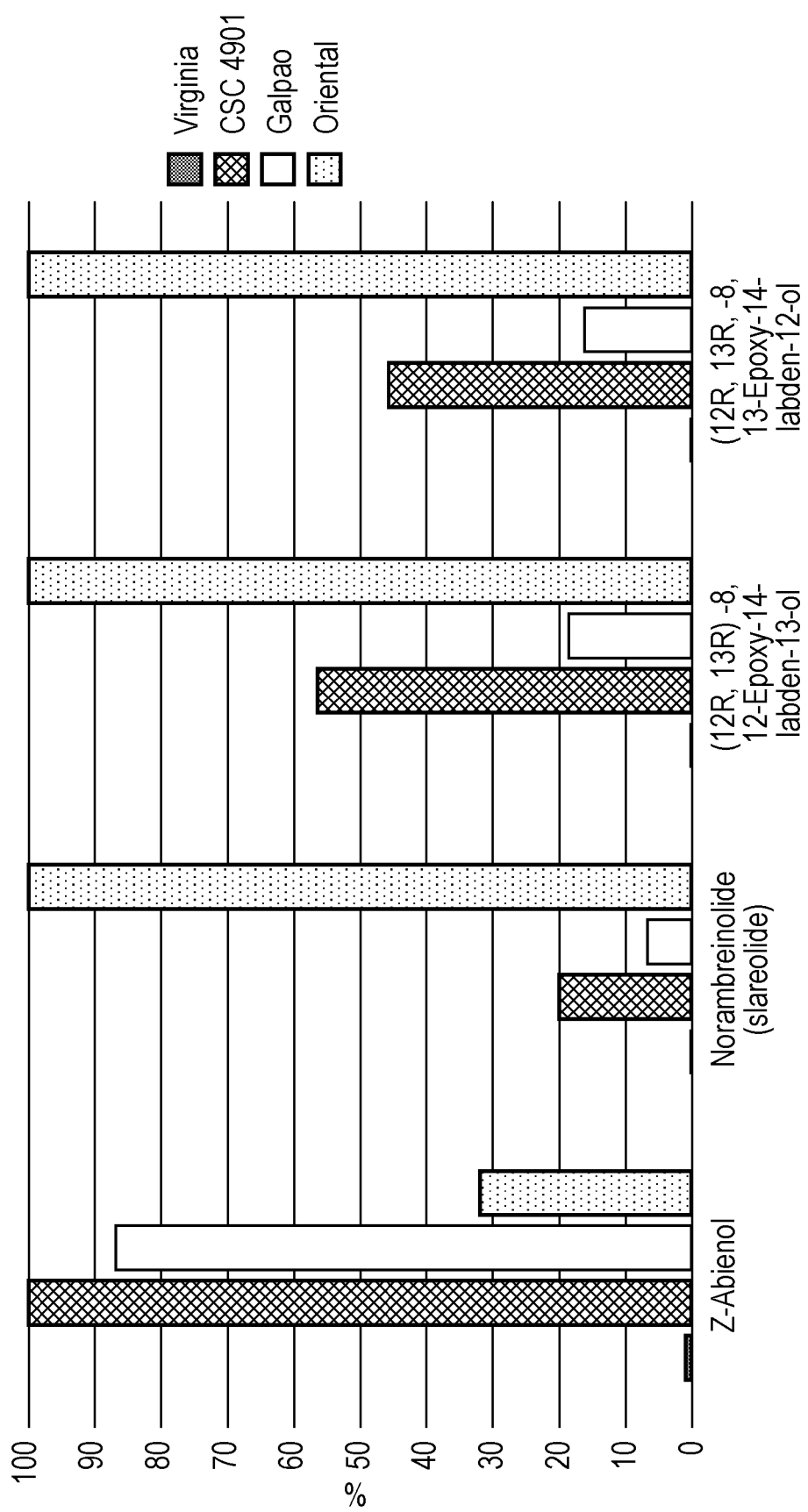
FIG. 4 illustrates the normalized distribution of Z-Abienol, Norambreinolide (sclareolide), (12R, 13R)-8,12-Epoxy-14-labden-13-ol and (12R, 13R)-8,13-Epoxy-14-labden-12-ol in different tobacco types: Galpão, Virginia, Oriental and CSC 4901.

However, as shown in the FIG. 4, the accumulation of Z-Abienol degradation products, mainly Norambreinolide, (12R, 13R)-8,12-Epoxy-14-labden-13-ol and (12R, 13R)-8,13-Epoxy-14-labden-12-ol, is higher CSC 4901 when compared to Galpao parent. In addition, hybrids of flue-cured and Oriental tobacco did not have higher levels of Z-Abienol degradation products compared to the Oriental tobacco (see FIG. 3).

Figure 5:
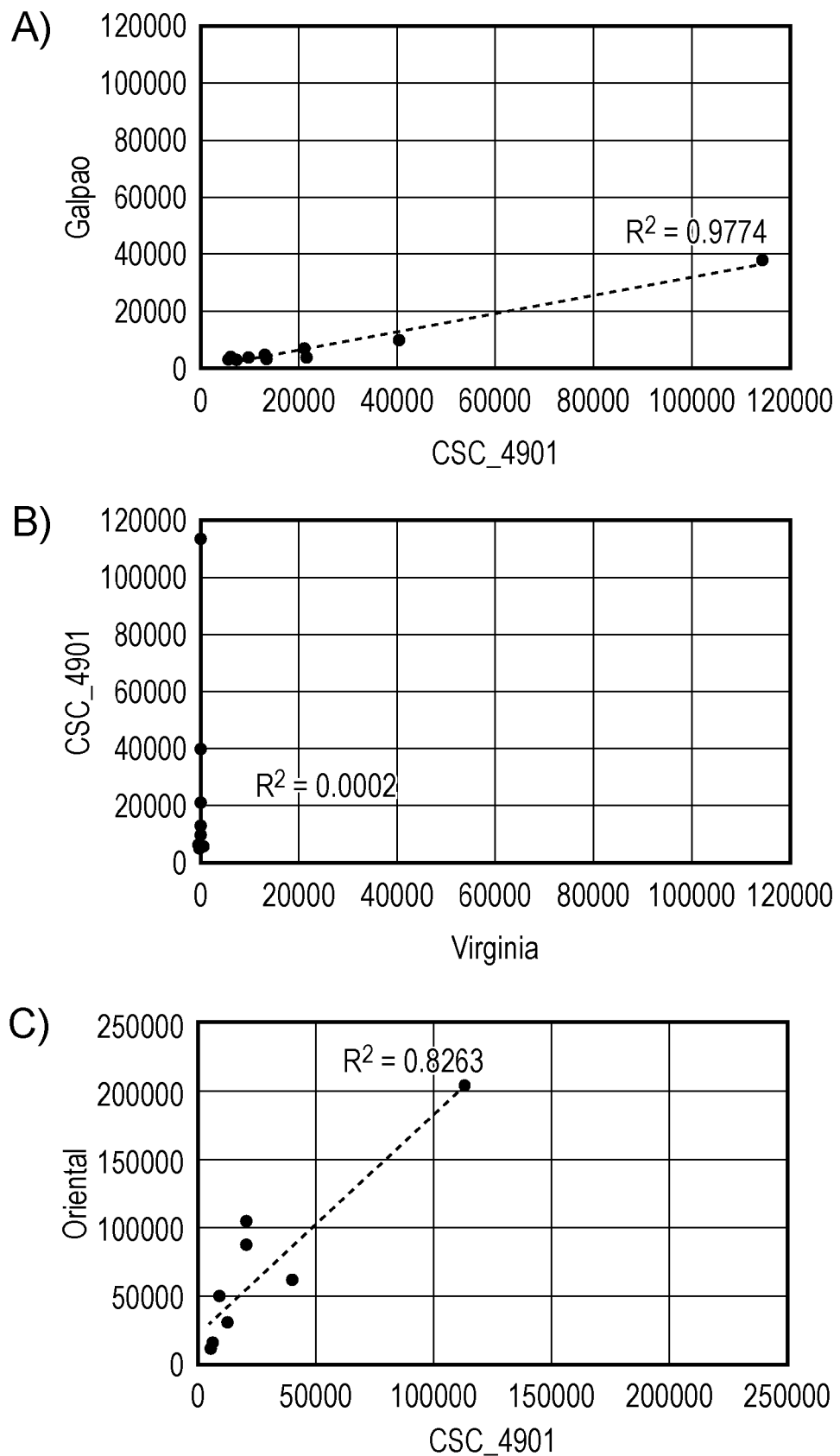
FIG. 5 illustrates the correlations between the profiles of Z-Abienol degradation products in: Galpao and CSC 4901 tobaccos (A); CSC 4901 and Virginia tobaccos (B); Oriental and CSC 4901 tobaccos (C). $R^2$=determination coefficient.

These degradation products are associated with cedar-amber notes (Davis & Nielson, M. T. (Eds.). Tobacco: Production, Chemistry, And Technology. Blackwell Science (Pub.), 1999) existent in the smoke of Oriental tobacco. Consequently, the higher content of Z-Abienol degradation products present in CSC 4901 compared to Virginia can explain the presence of aromatic notes in the hybrid tobacco. Moreover, the profile of Z-Abienol degradation products in CSC 4901 is more similar to that present in Galpão ($R^2$=0.98; FIG. 5A) and Oriental ($R^2$=0.83; FIG. 5C) than that present in Virginia ($R^2$=0.0002; FIG. 5B).

Figure 6:
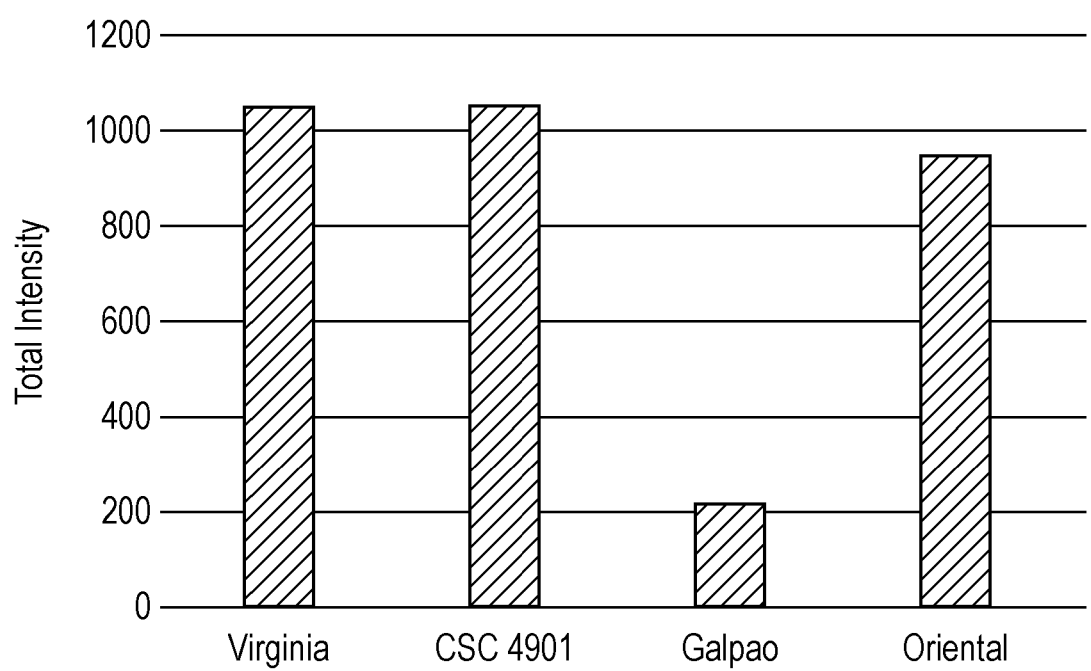
FIG. 6 illustrates the distribution of total polyphenols and carotenoids obtained from the sum of their individual components. in different tobacco types: Galpão, Virginia, Oriental and CSC 4901.
Figure 7:
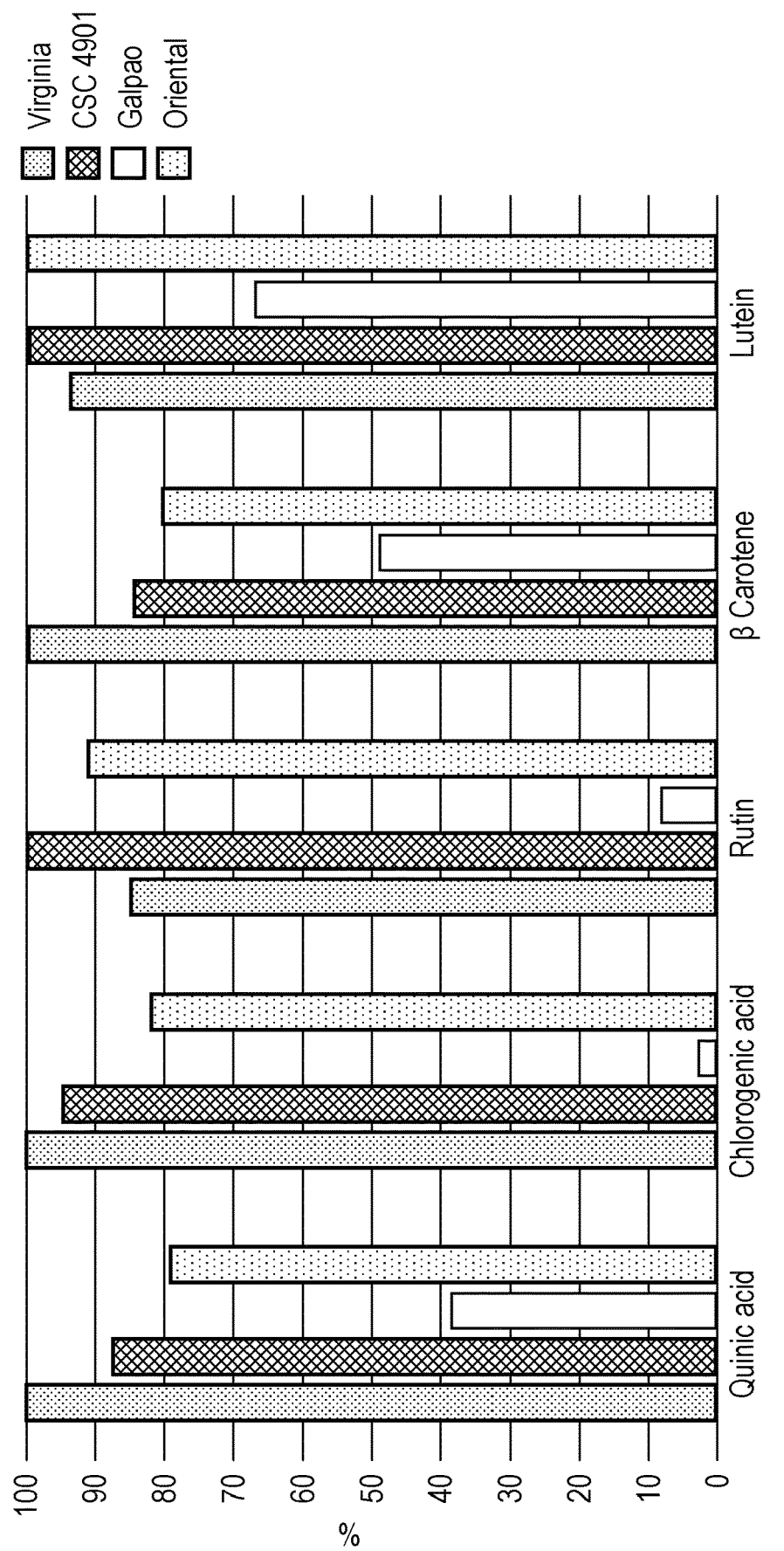
FIG. 7 illustrates the normalized distribution of Quinic acid, Chlorogenic acid, Rutin, β-carotene and Lutein in different tobacco types: Galpão, Virginia, Oriental and CSC 4901 (left to right).
Figure 8:
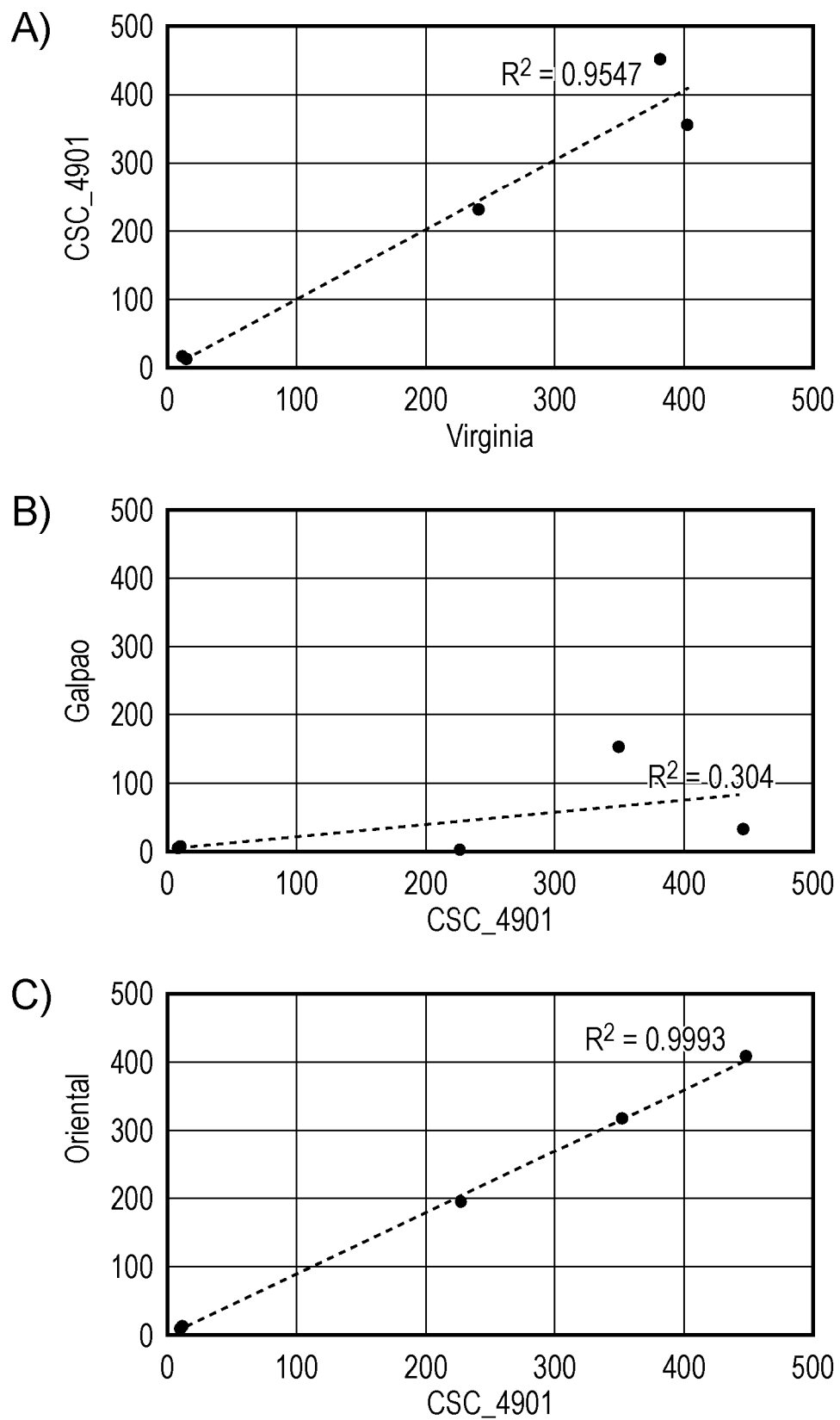
FIG. 8 illustrates the correlations between the profiles of polyphenols and carotenoids in: CSC 4901 and Virginia tobaccos (A); Galpao and CSC 4901 tobaccos (B); Oriental and CSC 4901 tobaccos (C). $R^2$=determination coefficient.

A comparison between the CSC 4901 and Galpao tobaccos was also carried out. As shown in the FIG. 6, the CSC 4901 has a high content of polyphenols and carotenoids when compared to Galpao, but similar to that in Virginia and Oriental. Moreover, as shown in the FIG. 7, the profiles of Quinic acid, Chlorogenic acid, Rutin, β-carotene and Lutein found in the CSC 4901 are quite similar to that in Virginia and Oriental tobacco. On the other hand, the profiles of these compounds in Galpao differs significantly from that in CSC 4901. The high determination coefficients obtained for the correlations between the profiles of polyphenols and carotenoids in CSC 4901 and Virginia ($R^2$=0.95; FIG. 8A) as well as in CSC 4901 and Oriental ($R^2$=0.99; FIG. 8C) compared to the weak correlation between Galpão and CSC 4901 ($R^2$ 0.30; FIG. 8B) agreed with these results.

A detailed description of chemical markers characterizing the CSC 4901 tobacco including their putative identification was performed by comparison of the measured and theoretical monoisotopic mass establishing a threshold of 10 ppm. Authentic analytical standards compounds were used to confirm the chemical identity of the selected compounds.

Biological Deposits

A deposit of at least 2500 seeds of parent varieties of tobacco hybrids disclosed above and recited in the appended claims have been made in accordance with the Budapest Treaty with American Type Culture Collection (ATCC), 10801 University Boulevard, Manassas, Va. 20110. The date of deposit for seeds representative of varieties Nicotiana tabacuum L; P10215428 was 10 Jan. 2017, under accession number PTA-123790 on behalf of Souza Cruz S.A, (Rua Candelaria, 66, Centro, Rio de Janeiro, RJ, Brazil, 20091-900). We hereby confirm that the depositor (Souza Cruz S.A) has authorised the applicant to refer to the deposited biological material in patent applications or patents and has given its unreserved and irrevocable consent to the deposited material being made available to the public.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

**BUDAPEST RESTRICTED CERTIFICATE OF DEPOSIT
BUDAPEST TREATY ON THE INTERNATIONAL RECOGNITION OF
THE DEPOSIT OF MICROORGANISMS FOR THE PURPOSES OF PATENT PROCEDURE
INTERNATIONAL FORM
RECEIPT IN THE CASE OF AN ORIGINAL DEPOSIT ISSUED PURSUANT TO RULE 7.3
AND VIABILITY STATEMENT ISSUED PURSUANT TO RULE 10.2**

The American Type Culture Collection (ATCC®) has received your deposit of seeds/strain(s)/strain(s) in connection with the filing of an application for patent. The following information is provided to fulfill Patent Office requirements.

**Oscar Pontes
Souza Cruz S.A.
Rua Candelaria, 66, Centro
Rio de Janeiro, RJ
Brazil 20091-900**

Deposited on Behalf of: Souza Cruz S.A.

Date of Receipt of seeds/strain(s) by the ATCC®: January 10, 2017

| Identification Reference by Depositor: | ATCC ®Patent Deposit Designation: | Quantity Received: |
|---|---|---|
| Nicotiana tabacum L; P10215428 | PTA-123790 | 1 vial |

The ATCC® understands that:

1. The deposit of these seeds/strain(s) does not grant ATCC® a license, either express or implied, to infringe the patent, and our release of these seeds/strain(s) to others does not grant them a license, either express or implied, to infringe the patent.

2. If the deposit should die or be destroyed during the effective term of the patent, it shall be your responsibility to replace it with viable material. It is also your responsibility to supply a sufficient quantity for distribution for the deposit term. ATCC® will distribute and maintain the material for 30 years or 5 years following the most recent request for the deposit, whichever is longer. The United States and many other countries are signatory to the Budapest Treaty.

Prior to the issuance of a U.S. Patent, the ATCC® agrees in consideration for a one-time service charge, not to distribute these seeds/strain(s) or any information relating thereto or to their deposit except as instructed by the depositor or relevant patent office. After relevant patent issues we are responsible to release the seeds/strain(s) and they will be made available for distribution to the public without any restrictions. We will inform you of requests for the seeds/strain(s) for 30 years from date of deposit.

The deposit was tested and on that February 6, 2017, the seeds/strain(s) were viable
International Depository Authority: American Type Culture Collection (ATCC®), Manassas, VA, USA
Signature of person having authority to represent ATCC®:
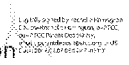
Rochelle
Harrington
———————————————————
ATCC® Patent Depository                                         February 7, 2017
cc: Aylsa Williams
Ref. or Docket No.: P109376GB

The invention claimed is:

1. A hybrid tobacco plant of variety Nicotiana tabacum L; P10215428 or a part thereof, grown from a seed representative of said variety, said representative seed having been deposited under ATCC Accession No. PTA-123790.

2. A seed of hybrid tobacco variety Nicotiana tabacum L; P10215428, wherein representative seed of said tobacco variety has been deposited under ATCC Accession No. PTA-123790.

3. A plant cell, a plant propagation material, or a harvested material of a hybrid tobacco plant or a part thereof as defined in claim 1.

4. Processed tobacco material comprising a harvested material or leaf from a hybrid tobacco plant as defined in claim 1.

5. The processed tobacco material according to claim 4, wherein the harvested material or leaf is processed by curing, fermentation, pasteurising or combinations thereof.

6. The processed tobacco material of claim 5, wherein said tobacco is flue-cured.

7. A tobacco blend comprising said tobacco material according to claim 4.

8. The tobacco blend of claim 7, wherein between approximately 25% and approximately 50% of said tobacco blend comprises tobacco material from said hybrid tobacco plant.

9. A tobacco product comprising the tobacco material of claim 4.

10. The tobacco product of claim 9, wherein said product is selected from the group consisting of a cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, shredded tobacco, and cut tobacco.

11. A population of the hybrid tobacco plant as defined in claim 1.

12. The hybrid plant according to claim 1, wherein said hybrid tobacco plant is male sterile.

13. A smoking article, smokeless tobacco product or tobacco heating device comprising a plant or a part thereof according to claim 1.

14. The harvested material of claim 3, wherein the harvested material is harvested leaf.

15. The processed tobacco material of claim 4, wherein the processed tobacco material is processed tobacco leaf.

16. The processed tobacco material of claim 15, wherein the processed tobacco leaf is non-viable processed tobacco leaf.

17. The processed tobacco material of claim 5, wherein the processed tobacco material is processed tobacco leaf.

18. The processed tobacco material of claim 6, wherein the processed tobacco material is processed tobacco leaf.

* * * * *